United States Patent
Kim et al.

(10) Patent No.: US 10,293,009 B2
(45) Date of Patent: May 21, 2019

(54) **PHARMACEUTICAL OR FOOD COMPOSITION COMPRISING *OLDENLANDIA BRACHYPODA*, *SPERGULARIA MARINA*, *DISPORUM SMILACINUM*, *PERSICARIA POSUMBU*, OR *GEUM ALEPPICUM***

(71) Applicant: KOREA FOOD RESEARCH INSTITUTE, Seongnam-si, Gyeonggi-do (KR)

(72) Inventors: Hye-Young Kim, Seoul (KR); Mee-Ra Rhyu, Seongnam-si (KR); Kyong Kim, Gwangju-si (KR); Min Park, Seoul (KR); Yu-Mi Lee, Gwangju (KR)

(73) Assignee: KOREA FOOD RESEARCH INSTITUTE, Seongnam-si, Gyeonggi-do (KR)

( * ) Notice: Subject to any disclaimer, the term of this patent is extended or adjusted under 35 U.S.C. 154(b) by 182 days.

(21) Appl. No.: 14/655,703

(22) PCT Filed: Nov. 12, 2013

(86) PCT No.: PCT/KR2013/010249
§ 371 (c)(1),
(2) Date: Jun. 25, 2015

(87) PCT Pub. No.: WO2014/104570
PCT Pub. Date: Jul. 3, 2014

(65) Prior Publication Data
US 2015/0352167 A1    Dec. 10, 2015

(30) Foreign Application Priority Data

Dec. 26, 2012 (KR) .................. 10-2012-0153650
Dec. 26, 2012 (KR) .................. 10-2012-0153651
Dec. 26, 2012 (KR) .................. 10-2012-0153652
Dec. 26, 2012 (KR) .................. 10-2012-0153653
Dec. 26, 2012 (KR) .................. 10-2012-0153654

(51) Int. Cl.
*A61K 36/70* (2006.01)
*A61K 36/73* (2006.01)
*A61K 36/00* (2006.01)
*A61K 36/185* (2006.01)
*A61K 36/748* (2006.01)
*A61K 36/896* (2006.01)
*A61K 36/36* (2006.01)
*A23L 33/105* (2016.01)

(52) U.S. Cl.
CPC .......... *A61K 36/185* (2013.01); *A23L 33/105* (2016.08); *A61K 36/36* (2013.01); *A61K 36/70* (2013.01); *A61K 36/73* (2013.01); *A61K 36/748* (2013.01); *A61K 36/896* (2013.01); *A23V 2002/00* (2013.01)

(58) Field of Classification Search
None
See application file for complete search history.

(56) References Cited

U.S. PATENT DOCUMENTS

2005/0064049 A1    3/2005  Mori et al.

FOREIGN PATENT DOCUMENTS

| CN | 101947265 A | * | 1/2011 |
|----|-------------|---|--------|
| JP | 2002-255804 A | | 9/2002 |
| KR | 10-0718602 B1 | | 6/2007 |
| KR | 10-0811864 B1 | | 3/2008 |
| WO | 2010-010949 A1 | | 1/2010 |

OTHER PUBLICATIONS

Heo et al. (2009) Korean J. Community Living Science. 20(2): 181-191.*
Jouad et al. (2001) J. Ethnopharmacology 76: 159-163.*
Karadeniz et al. (2014) Prey. Nutr. Food Sci. 19(3): 187-193.*
Lee et al. (2014) J. Med. Food 17 (11): 1197-1203.*
Raskin et al. (2004) Current Pharmaceutical Design, 10, 3419-3429.*
Revilla et al. (1998) J. Agric. Food Chem. 46, 4592-4597.*
Tomassi et al. (1998) J. Nat. Prod. 61, 323-327.*
Vinholes et al. (2011) Food Chemistry 129; 454-462.*
Cheng et al. (2011) Chemistry and Biodiversity, vol. 8 203-222. (Year: 2011).*
International Search Report dated Apr. 29, 2014 of PCT/KR2013/010249 which is the parent application and its English translation—8 pages.
Xu et al., "Chemical Constituents and Pharmacological Activities of Hedyotis diffusa", Natural Product Sciences, 2005, vol. 11, No. 1, pp. 1-9.

(Continued)

*Primary Examiner* — Christopher R Tate
*Assistant Examiner* — Russell G Fiebig
(74) *Attorney, Agent, or Firm* — Knobbe Martens Olson & Bear LLP

(57) ABSTRACT

The present disclosure relates to a pharmaceutical composition or a food composition which has excellent activity of stimulating enteroendocrine cells while being safe with few side effects. The composition contains one or more of an *Oldenlandia brachypoda* extract, a *Spergularia marina* extract, a *Disporum smilacinum* extract, a *Persicaria posumbu* extract and a *Geum aleppicum* extract as an active ingredient. The composition of the present disclosure can be usefully used as a pharmaceutical composition or a food composition for preventing, improving or treating diabetes mellitus, improving or treating heart diseases, improving or treating arteriosclerosis, improving or treating digestive disorders and malabsorption, preventing or treating obesity or suppressing appetite, protecting nerves, treating or improving liver diseases, and so forth. In addition, the composition of the present disclosure can promote the secretion of GLP-1, CCK or 5-HT, affect the activation of hTGR5 and act as TRP, TRPA1, G protein and PLCβ2 agonists.

8 Claims, 4 Drawing Sheets

(56) References Cited

OTHER PUBLICATIONS

Jouad et al., "Cholesterol-lowering activity of the aqueous extract of Spergularia purpurea in normal and recent-onset diabetic rats", Journal of Ethnopharmacology, 2003, vol. 87, pp. 43-49.
Jouad et al., "Hypoglycaemic effect of Spergularia purpurea in normal and streptozotocin-induced diabetic rats", Journal of Ethnopharmacology, 2000, vol. 71, pp. 169-177.
Mourad et al., "Neural regulation of intestinal nutrient absorption", Progress in Neurobiology, 2011, vol. 95, pp. 149-162.
Campbell et al., "Pharmacology, Physiology, and Mechanisms of Incretin Hormone Action", Cell Metabolism, 2013, vol. 17, pp. 819-837.
Burgmaier et al., "Glucagon-like peptide-1 (GLP-1) and its split products GLP-1(9-37) and GLP-1(28-37) stabilize atherosclerotic lesions in apoe -/- mice", Atherosclerosis, 2013, vol. 231, pp. 427-435.
Salcedo et al., "Neuroprotective and neurotrophic actions of glucagon-like peptide-1: an emerging opportunity to treat neurodegenerative and cerebrovascular disorders", British Journal of Pharmacology, 2012, vol. 166, pp. 1586-1599.
Sokos et al., "Glucagon-Like Peptide-1 Infusion Improves Left Ventricular Ejection Fraction and Functional Status in Patients With Chronic Heart Failure", Journal of Cardiac Failure, 2006, vol. 12, pp. 694-699.
Ban et al., "Cardioprotective and Vasodilatory Actions of Glucagon-Like Peptide 1 Receptor Are Mediated Through Both Glucagon-Like Peptide 1 Receptor-Dependent and -Independent Pathways", Circulation, 2008, vol. 117, pp. 2340-2350.
Reimann et al., "Glucose Sensing in L Cells: A Primary Cell Study", Cell Metabolism, 2008, vol. 8, pp. 532-539.
Lauffer et al., "GPR119 Is Essential for Oleoylethanolamide-Induced Glucagon-Like Peptide-1 Secretion From the Intestinal Enteroendocrine L-Cell", Diabetes, 2009, vol. 58, pp. 1058-1066.
Jang et al., "Gut-expressed gustducin and taste receptors regulate secretion of glucagon-like peptide-1", PNAS, 2007, vol. 104, No. 38, pp. 15069-15074.
Lieu et al., "GPBA: a GPCR for bile acids and an emerging therapeutic target for disorders of digestion and sensation", British Journal of Pharmacology, 2014, vol. 171, pp. 1156-1166.
Pols et al., "TGR5 Activation Inhibits Atherosclerosis by Reducing Macrophage Inflammation and Lipid Loading", Cell Metabolism, 2011, vol. 14, pp. 747-757.
Purhonen et al., "TRPA1 channel activation induces cholecystokinin release via extracellular calcium", FEBS Letters, 2008, vol. 582, pp. 229-232.
Gershon et al., "The Serotonin Signaling System: From Basic Understanding to Drug Development for Functional GI Disorders", Gastroenterology, 2007, vol. 132, No. 1, pp. 397-414.

* cited by examiner

PHARMACEUTICAL OR FOOD COMPOSITION COMPRISING *OLDENLANDIA BRACHYPODA, SPERGULARIA MARINA, DISPORUM SMILACINUM, PERSICARIA POSUMBU,* OR *GEUM ALEPPICUM*

TECHNICAL FIELD

The present disclosure relates to a pharmaceutical composition or a food composition. More particularly, the present disclosure relates to a pharmaceutical composition or a food composition which contains an extract that promotes the secretion of gut hormones or neuropeptides from enteroendocrine cells as an active ingredient and, thus, is useful for specific diseases or disorders.

This application claims the priority of Korean Patent Application Nos. 10-2012-0153650, 10-2012-0153651, 10-2012-0153652, 10-2012-0153653 and 10-2012-0153654 filed on Dec. 26, 2012, the disclosures described in the specifications and drawings of which are incorporated herein by reference.

BACKGROUND TECHNOLOGY

Enteroendocrine cells, which are endocrine cells present in the epithelium in the gastrointestinal tract, secrete gut hormones or neuropeptides in response to stimuli by the substances introduced into the intestinal lumen. The same substances secreted by them are called hormones if they act on target organs by being transported there via the bloodstream or neuropeptides if they act as signaling molecules for activation of vagus nerves.

The gut hormones or neuropeptides secreted by the enteroendocrine cells include glucagon-like peptide-1 (GLP-1), cholecystokinin (CCK), serotonin (5-hydroxytryptamine, 5-HT), etc.

First, GLP-1 is secreted by L cells which are enteroendocrine cells present in the ileum and the colon.

GLP-1 is known to be effective in treating diabetes mellitus, treating obesity, treating heart diseases, regulating secretion and absorption of digestive enzymes [Mourad F H & Saade N E, Neural regulation of intestinal nutrient absorption. *Progress in Neurobiology* (2011) 95, 149-162], enhancing immunity [Campbell J E and Drucker D J, Pharmacology, physiology, and mechanisms of incretin hormone action. *Cell Metabolism* (2013) 17, 819], treating arteriosclerosis [Burgmaier M et al., Glucagon-like peptide-1 (GLP-1) and its split products GLP-1(9-37) and GLP-1(28-37) stabilize atherosclerotic lesions in apoe mice. *Atherosclerosis* (2013) 231, 427-435], treating cerebrovascular diseases and neuroinflammation (Salcedo I et al., Neuroprotective and neurotrophic actions of glucagon-like peptide-1 (GLP-1): an emerging opportunity to treat neurodegenerative and cerebrovascular disorders. *British Journal of Pharmacology* (2012) 166, 1586-1599), and so forth.

It is involved in the treatment of diabetes through glucose-dependent stimulation of insulin secretion, increase of Insulin gene expression, promotion of proliferation of pancreatic beta cells, enhancement of survival of pancreatic beta cells, suppression of glucagon secretion, decrease of blood sugar level, etc. in the pancreas. Also, it is involved in the treatment of obesity by slowing the gastric emptying rate, suppressing appetite, increasing satiety and suppressing food intake.

In addition, it is known to be effective in treating heart diseases by protecting cardiomyocytes from ischemia and improving heart functions of patients and be involved in the regulation of digestion and absorption through secretion of digestive enzymes in the pancreas and the small intestine (Sokos, G. G. et al., Glucagon-like peptide-1 infusion improves left ventricular ejection fraction and functional status in patients with chronic heart failure. *J. Card. Fail.* (2006) 12. 694-699., Ban, K., et al., Cardioprotective and vasodilatory actions of glucagon-like peptide-1 receptor are mediated through both glucagon-like peptide-1 receptor-dependent and -independent pathways. *Circulation* (2008) 117: 2340-2350).

It is known that the secretion of GLP-1 is promoted by the activation of TGR5 (C protein-coupled bile acid receptor 131, GPR131) and GPR119 (G-protein coupled receptor 119) which are G protein-coupled receptors (GPCRs) (Reimann, F., et al., Glucose sensing in L cells: a primary cell study. Cell Metab. (2008) 8: 532-539; Lauffer, L. M., et al., GPR119 is essential for oleoylethanolamide-induced glucagon-like peptide-1 secretion from the intestinal enteroendocrine L cell. Diabetes (2009) 58:1058-1066) or by the activation of α-gustducin (Jang, H. J., et al., 2007. Gut expressed gustducin and taste receptors regulate secretion of glucagon-like peptide-1. Proceeding of the National Academy of Science 104, 15069-15074.). In particular, it is known that the activation of the G protein-coupled receptor (GPCR) TGR5 (G protein-coupled bile acid receptor 131, GPR131) expressed in brown adipose tissue and muscle is effective in treating obesity by increasing energy consumption and is related with the improvement of liver diseases (Lieu T et al., GPBA: A G protein-coupled receptor for bile acids and an emerging therapeutic target for disorders of digestion and sensation. British Journal of Pharmacology (2014) in press) and suppresses arteriosclerosis (Pols T W H et al., TGR5 activation inhibits atherosclerosis by reducing macrophage inflammation and lipid loading. Cell Metabolism (2011) 14, 747).

Next, CCK is synthesized and secreted by I-cells which are enteroendocrine cells present in the duodenum and the jejunum. Being secreted in the duodenal mucosa, CCK is known to induce anti-diabetic effect by suppressing glucose production through activation of the CCK-A receptor on the vagus nerves, provide anti-obesity effect by suppressing food intake and be involved in the regulation of digestion and absorption.

It is known that G protein-coupled receptors (GPCRs) and signaling molecules (G proteins, PLCβ2 (phospholipase Cβ2)), transient receptor potential (TRP) channels, etc. are involved in the secretion of CCK (*FEBS Letters* (2008) 582: 229-232).

And, 5-HT, which is a hormone secreted by enterochromaffin (EC) cells present in the whole gastrointestinal tract, is known to be involved in the regulation of digestion and absorption and provide anti-obesity effect by suppressing appetite (Gershon, M. D., Tack, J. (2007) The serotonin signaling system: from basic understanding to drug development for functional GI disorders. *Gastroenterology* 132, 397-414).

It is known that the secretion of gut hormones or neuropeptides plays a role in maintaining homeostasis related with food intake and digestive action (intestinal motility, secretion of digestive enzymes, appetite control, etc.). The homeostasis refers to the balance between the energies absorbed and consumed. If the balance is broken, it may cause diabetes, cardiovascular diseases, etc.

Globally, there have been consistent efforts to develop drugs effective for diabetes, cardiovascular diseases and other severe diseases. However, it is not easy to develop a drug which is very effective but has few side effects such as obesity, hepatotoxicity and edema.

Meanwhile, although drugs having anti-obesity effect are used for prevention or treatment of obesity, these drugs are known to induce side effects such as oily stools, abdominal inflation, dizziness, dry mouth, constipation, increased blood pressure, etc. Accordingly, development of natural functional substances which are safer and have stronger efficacy is required.

DISCLOSURE

Technical Problem

The present disclosure is directed to providing a pharmaceutical composition or a food composition which exhibits various useful effects with excellent activity of stimulating enteroendocrine cells while being safe with few side effects.

In particular, the present disclosure is directed to providing a pharmaceutical composition or a food composition which exhibits one or more effect of treating diabetes, suppressing appetite, preventing obesity, improving heart diseases, improving digestion and malabsorption, improving arteriosclerosis, protecting nerves and treating or improving liver diseases.

The present disclosure is also directed to providing a method for achieving one or more effect of treating diabetes, suppressing appetite, preventing obesity, improving heart diseases, improving digestion and malabsorption, improving arteriosclerosis, protecting nerves and treating or improving liver diseases in an individual or a patient in need thereof, by administering an effective amount of a pharmaceutical composition or a food composition containing a safe extract as an active ingredient to the individual or the patient.

The present disclosure is also directed to providing a composition which stimulates the secretion of GLP-1, CCK or 5-HT or affects the activation of hTGR5 and, as a result, acts as a TRP, TRPA1, G protein or PLCβ2 agonist.

Technical Solution

In an aspect, the present disclosure provides a composition containing one or more of an *Oldenlandia brachypoda* extract, a *Spergularia marina* extract, a *Disporum smilacinum* extract, a *Persicaria posumbu* extract and a *Geum aleppicum* extract as an active ingredient, which has an activity of stimulating enteroendocrine cells and, as a result, exhibits the effect of treating diabetes, suppressing appetite, preventing obesity, improving heart diseases, improving digestion and malabsorption, improving arteriosclerosis, protecting nerves and treating or improving liver diseases.

The inventors of the present disclosure have identified that, among the natural products the safety of which has been proven through use for a long time, one or more extract of an *Oldenlandia brachypoda* extract, a *Spergularia marina* extract, a *Disporum smilacinum* extract, a *Persicaria posumbu* extract and a *Geum aleppicum* extract is effective in secreting gut hormones and/or neuropeptides by activating enteroendocrine cells and have completed the present disclosure.

The inventors of the present disclosure have experimentally identified that one or more extract of an *Oldenlandia brachypoda* extract, a *Spergularia marina* extract, a *Disporum smilacinum* extract, a *Persicaria posumbu* extract and a *Geum aleppicum* extract can exhibit the effect of increasing the expression of the insulin gene, inhibiting the secretion of glucagon, lowering blood sugar, etc. Accordingly, the present disclosure provides a use of the extract for preventing and improving diabetes.

The inventors of the present disclosure have also experimentally identified that one or more extract of an *Oldenlandia brachypoda* extract, a *Spergularia marina* extract, a *Disporum smilacinum* extract, a *Persicaria posumbu* extract and a *Geum aleppicum* extract exhibits the effect of suppressing appetite and increasing satiety. Accordingly, the present disclosure provides a use of the extract for preventing obesity by suppressing appetite.

The inventors of the present disclosure have also experimentally identified that one or more extract of an *Oldenlandia brachypoda* extract, a *Spergularia marina* extract, a *Disporum smilacinum* extract, a *Persicaria posumbu* extract and a *Geum aleppicum* extract promotes the secretion of digestive enzymes in the pancreas and the small intestine and regulates intestinal contraction and motility. Accordingly, the present disclosure provides a use of the extract for improving digestion and malabsorption.

The inventors of the present disclosure have also experimentally identified that one or more extract of an *Oldenlandia brachypoda* extract, a *Spergularia marina* extract, a *Disporum smilacinum* extract, a *Persicaria posumbu* extract and a *Geum aleppicum* extract exhibits an excellent effect of protecting cardiomyocytes by controlling bloodstream to the cardiac muscle. Accordingly, the present disclosure provides a use of the extract for improving heart diseases. More specifically, the one or more extract of an *Oldenlandia brachypoda* extract, a *Spergularia marina* extract, a *Disporum smilacinum* extract, a *Persicaria posumbu* extract and a *Geum aleppicum* extract of the present disclosure may exhibit an effect of protecting cardiomyocytes from ischemia and improving the cardiac functions of a patient with a concern of heart failure.

The inventors of the present disclosure have also experimentally identified that one or more extract of an *Oldenlandia brachypoda* extract, a *Spergularia marina* extract, a *Disporum smilacinum* extract, a *Persicaria posumbu* extract and a *Geum aleppicum* extract can prevent arteriosclerosis. Accordingly, the present disclosure provides a use of the extract for improving arteriosclerosis.

The inventors of the present disclosure have also experimentally identified that one or more extract of an *Oldenlandia brachypoda* extract, a *Spergularia marina* extract, a *Disporum smilacinum* extract, a *Persicaria posumbu* extract and a *Geum aleppicum* extract activates the arcuate nucleus (ARC) in the hypothalamus of the brain and activates the vagus nerves. Accordingly, the present disclosure provides a use of the extract for protecting nerves.

More specifically, the one or more extract of an *Oldenlandia brachypoda* extract, a *Spergularia marina* extract, a *Disporum smilacinum* extract, a *Persicaria posumbu* extract and a *Geum aleppicum* extract of the present disclosure may exhibit an effect of treating neurodegenerative diseases and cerebrovascular diseases, treating neuroinflammation and promoting neurogenesis.

In another embodiment, the present disclosure provides a use of one or more extract of an *Oldenlandia brachypoda* extract, a *Spergularia marina* extract, a *Disporum smilacinum* extract, a *Persicaria posumbu* extract and a *Geum aleppicum* extract for treating or improving liver diseases. More specifically, the one or more extract of an *Oldenlandia brachypoda* extract, a *Spergularia marina* extract, a *Disporum smilacinum* extract, a *Persicaria posumbu* extract and a *Geum aleppicum* extract of the present disclosure may exhibit an effect of reducing hepatic inflammation, enhancing enterohepatic blood flow, improving hepatic functions, treating cholestatic liver diseases, treating pruritus and painless jaundice, improving intestinal functions and promoting neurotransmission.

In another aspect, the present disclosure provides a composition which stimulates or affects the secretion of GLP-1, CCK or 5-HT or acts as a TRP, TRPA1, G protein or PLCβ2 agonist.

Specifically, the inventors of the present disclosure have experimentally identified that one or more extract of an *Oldenlandia brachypoda* extract, a *Spergularia marina* extract, a *Disporum smilacinum* extract, a *Persicaria posumbu* extract and a *Geum aleppicum* extract stimulates the secretion of GLP-1. Accordingly, the present disclosure provides a use of the extract for stimulating the secretion of GLP-1.

The inventors of the present disclosure have also experimentally identified that one or more extract of an *Oldenlandia brachypoda* extract, a *Spergularia marina* extract, a *Disporum smilacinum* extract, a *Persicaria posumbu* extract and a *Geum aleppicum* extract stimulates the secretion of CCK and activates GPCRs by increasing the intracellular level of calcium and cAMP. Accordingly, the present disclosure provides a use of the extract for stimulating the secretion of CCK.

The inventors of the present disclosure have also experimentally identified that one or more extract of an *Oldenlandia brachypoda* extract, a *Spergularia marina* extract, a *Disporum smilacinum* extract, a *Persicaria posumbu* extract and a *Geum aleppicum* extract stimulates the secretion of 5-HT and induces the change in the intracellular level of calcium. Accordingly, the present disclosure provides a use of the extract for stimulating the secretion of 5-HT.

In another aspect, the present disclosure provides a composition which acts as a TRP, TRPA1, G protein or PLCβ2 agonist.

Specifically, the inventors of the present disclosure have experimentally identified that one or more extract of an *Oldenlandia brachypoda* extract, a *Spergularia marina* extract, a *Disporum smilacinum* extract, a *Persicaria posumbu* extract and a *Geum aleppicum* extract activates TGR5. Accordingly, the present disclosure provides a use of the extract for activating TGR5.

The inventors of the present disclosure have also experimentally identified that one or more extract of an *Oldenlandia brachypoda* extract, a *Spergularia marina* extract, a *Disporum smilacinum* extract, a *Persicaria posumbu* extract and a *Geum aleppicum* extract increases calcium level and activates TRP (transient receptor potential) channels and TRPA1 (transient receptor potential cation channel, member A1). Accordingly, the present disclosure provides a use of the extract for activating the TRP and TRPA1 channels. The inventors of the present disclosure have also experimentally identified that one or more extract of an *Oldenlandia brachypoda* extract, a *Spergularia marina* extract, a *Disporum smilacinum* extract, a *Persicaria posumbu* extract and a *Geum aleppicum* extract increases intracellular level of calcium ion by activating G protein. Accordingly, the present disclosure provides a use of the extract for activating G protein.

The inventors of the present disclosure have also experimentally identified that one or more extract of an *Oldenlandia brachypoda* extract, a *Spergularia marina* extract, a *Disporum smilacinum* extract, a *Persicaria posumbu* extract and a *Geum aleppicum* extract increases intracellular level of calcium ion and cAMP by activating PLCβ2. Accordingly, the present disclosure provides a use of the extract for activating PLCβ2.

The one or more extract of an *Oldenlandia brachypoda* extract, a *Spergularia marina* extract, a *Disporum smilacinum* extract, a *Persicaria posumbu* extract and a *Geum aleppicum* extract of the present disclosure means an extract obtained by a method commonly employed in the art to which the present disclosure belongs and may be further purified after the extraction through fractionation, separation, filtration, etc.

For example, the *Oldenlandia brachypoda* extract, the *Spergularia marina* extract, the *Disporum smilacinum* extract, the *Persicaria posumbu* extract and the *Geum aleppicum* extract according to the present disclosure may be solvent extracts of the corresponding plants or dried products thereof. For the extraction of the plant extracts, any solvent used for extraction of natural products may be used as an extraction solvent without limitation. For example, purified water, a $C_1$-$C_4$ lower alcohol such as methanol, ethanol, propyl alcohol, butyl alcohol, etc. a polyhydric alcohol such as glycerin, butylene glycol, propylene glycol, etc. a hydrocarbon solvent such as methyl acetate, ethyl acetate, acetone, benzene, hexane, diethyl ether, dichloromethane, etc., or a mixture solvent thereof may be used. Specifically, purified water, a $C_1$-$C_4$ lower alcohol such as methanol, ethanol, propyl alcohol and butyl alcohol, or a mixture solvent thereof may be used. More specifically, purified water, ethanol or a mixture solvent thereof may be used. Further more specifically, a mixture solvent of purified water and ethanol may be used.

The amount of the extraction solvent may be 10-100 times, specifically 20-80 times, more specifically 30-50 times, based on the weight of one or more selected from *Oldenlandia brachypoda*, *Spergularia marina*, *Disporum smilacinum*, *Persicaria posumbu* and *Geum aleppicum*, although not being limited thereto.

The extract may be extracted according to an extraction method commonly employed in the art, such as stirring extraction, cold precipitation extraction, hot water extraction, immersion extraction, supercritical extraction, subcritical extraction, high-temperature extraction, high-pressure extraction, reflux extraction, ultrasonic extraction, etc. Specifically, reflux extraction under elevated temperatures or extraction at room temperature may be employed. The extraction may be performed specifically at 10-30° C. specifically for 1-20 days, more specifically for 1-5 days, although not being limited thereto.

More specifically, the extract may be prepared by drying one or more selected from *Oldenlandia brachypoda*, *Spergularia marina*, *Disporum smilacinum*, *Persicaria posumbu* and *Geum aleppicum* in the shade, pulverizing the same, performing extraction by adding an extraction solvent 1-20 times the volume of the pulverized plant and, optionally, performing concentration (under reduced pressure), drying or purification. More specifically, the active ingredient may be extracted using an extraction solvent as described above, either by (a) heating 1-20 hours at 50-100° C. using a cooling condenser in order to prevent evaporation of the solvent, or by (b) immersing at 5-37° C. for 1-15 days.

In another embodiment of the present disclosure, the extract for activating enteroendocrine cells may be a fraction of one or more selected from an *Oldenlandia brachypoda* extract, a *Spergularia marina* extract, a *Disporum smilacinum* extract, a *Persicaria posumbu* extract and a *Geum aleppicum* extract.

The fraction of the present disclosure may be obtained by fractionating one or more selected from the *Oldenlandia brachypoda* extract, the *Spergularia marina* extract, the *Disporum smilacinum* extract, the *Persicaria posumbu* extract and the *Geum aleppicum* extract (specifically a $C_1$-$C_4$ lower alcohol extract) with a solvent which is less polar than water, such as hexane, chloroform, butanol and ethyl acetate, specifically hexane or chloroform, although not being limited thereto.

Specifically, the extract according to the present disclosure may be a hexane or chloroform fraction of a $C_1$-$C_4$ lower alcohol extract.

The fraction may be obtained by using an extract in liquid state before drying or suspending or dissolving a dried extract in an appropriate solvent such as water, ethanol or a mixture solvent thereof, sequentially adding a solvent which is less polar than water, such as hexane, chloroform, butanol or ethyl acetate, and then concentrating under reduced pressure and/or drying the resulting separated layers.

Specifically, the concentration under reduced pressure may be performed using a vacuum rotary evaporator, although not being limited thereto.

And, the "drying" in the present disclosure may be drying under reduced pressure, vacuum drying, boiling drying, spray drying, drying at room temperature or freeze drying, specifically freeze drying. However, the present disclosure is not limited to these drying methods.

The one or more selected from an *Oldenlandia brachypoda* extract, a *Spergularia marina* extract, a *Disporum smilacinum* extract, a *Persicaria posumbu* extract and a *Geum aleppicum* extract according to the present disclosure has been found to activate enteroendocrine cells that secrete gut hormones and/or neuropeptides such as glucagon-like peptide-1 (GLP-1, GLP-1-(7-36) amide), cholecystokinin (CCK), serotonin (5-hydroxytryptamine, 5-HT), etc. and, thus, to promote the secretion of the gut hormones and/or the neuropeptides.

Accordingly, the present disclosure may provide a pharmaceutical composition which exhibits an effect of treating diabetes, suppressing appetite, preventing obesity, improving heart diseases, improving digestion and malabsorption, improving arteriosclerosis, protecting nerves or treating or improving liver diseases through promoted secretion of gut hormones and neuropeptides by the one or more selected from an *Oldenlandia brachypoda* extract, a *Spergularia marina* extract, a *Disporum smilacinum* extract, a *Persicaria posumbu* extract and a *Geum aleppicum* extract and activation of the gut hormones and/or the neuropeptides.

The present disclosure may also provide a food composition for treating diabetes, suppressing appetite, preventing obesity, improving heart diseases, improving digestion and malabsorption, improving arteriosclerosis, protecting nerves or treating or improving liver diseases, which contains one or more selected from an *Oldenlandia brachypoda* extract, a *Spergularia marina* extract, a *Disporum smilacinum* extract, a *Persicaria posumbu* extract and a *Geum aleppicum* extract as an active ingredient.

That is to say, the composition according to the present disclosure may be used as a medicinal drug, a health food supplement, a food additive, a feed additive, etc., although not being limited thereto.

The pharmaceutical composition of the present disclosure may further contain an adequate carrier, excipient or diluent commonly used to prepare drugs. The pharmaceutical composition according to the present disclosure may be formulated into formulations for oral administration such as powder, granule, tablet, capsule, suspension, emulsion, syrup, aerosol, etc. or into formulation for external application, suppository or sterile solution for injection, according to commonly employed methods. Examples of the carrier, excipient or diluent that may be contained in the pharmaceutical composition of the present disclosure may include lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate and mineral oil. For the formulation, a commonly used diluent or excipient such as filler, thickener, binder, wetting agent, disintegrant, surfactant, etc. may be used. Solid formulations for oral administration include tablet, pill, powder, granule, capsule, etc. The solid formulation is prepared by mixing the composition of the present disclosure with at least one excipient, e.g., starch, calcium carbonate, sucrose, lactose, gelatin, etc. In addition to simple excipients, a lubricant such as magnesium stearate and talc may also be added. Liquid formulations for oral administration include suspension, liquid for internal use, emulsion, syrup, etc. In addition to simple diluents such as water and liquid paraffin, various other excipients, e.g., wetting agent, sweetener, aromatic, preservative, etc., may be included. Formulations for parenteral administration include sterilized aqueous solution, non-aqueous solution, suspension, emulsion, lyophilized preparation and suppository. Examples of the non-aqueous solution or suspension may include propylene glycol, polyethylene glycol, vegetable oil such as olive oil, injectable ester such as ethyl oleate, and so forth. As a base of a suppository, witepsol, macrogol, Tween 61, cocoa butter, laurin butter, glycerogelatin, etc. may be used.

More specifically, a powder may be prepared, for example, by simply mixing the extract of the present disclosure with a pharmaceutically acceptable adequate excipient such as lactose, starch, microcrystalline cellulose, etc. A granule may be prepared by wet granulation using a solvent such as water, ethanol, isopropanol, etc. or by dry granulation using compressive force after mixing the extract of the present disclosure with a pharmaceutically acceptable adequate excipient and a pharmaceutically acceptable suitable binder such as polyvinylpyrrolidone, hydroxypropyl cellulose, etc. And, a tablet may be prepared by mixing the granule with a pharmaceutically acceptable suitable lubricant such as magnesium stearate and then tableting using a tablet machine.

The composition of the present disclosure may be in administered by oral administration, injection (e.g., intramuscular injection, intraperitoneal injection, intravenous injection, infusion, subcutaneous injection, implantation), inhalation, nasal administration, intravaginal administration, rectal administration, sublingual administration, transdermal administration, topical administration, etc. depending on the disease to be treated and the condition of the individual, although not being limited thereto. Depending on the administration route, a commonly used nontoxic, pharmaceutically acceptable carrier, additive or vehicle may be used to prepare a suitable dosage unit form. A depot formulation that can continuously release a drug for a predetermined time is also included in the scope of the present disclosure.

In order to achieve the purposes of the present disclosure, the one or more selected from an *Oldenlandia brachypoda* extract, a *Spergularia marina* extract, a *Disporum smilacinum* extract, a *Persicaria posumbu* extract and a *Geum aleppicum* extract the present disclosure may be administered in an amount of from about 0.001 mg/kg to about 10 g/kg every day. Specifically, the daily dose may be from about 0.01 mg/kg to about 1 g/kg. However, the administration dose may vary depending on the purity of the extract, the condition of a patient (age, sex, body weight, etc.), the severity of the condition to be treated, or the like. If necessary, a total daily administration dose may be divided and given several times a day.

When the one or more selected from an *Oldenlandia brachypoda* extract, a *Spergularia marina* extract, a *Disporum smilacinum* extract, a *Persicaria posumbu* extract and a *Geum aleppicum* extract of the present disclosure is used for a food composition, the type of food is not particularly limited. Examples of the food to which the extract can be added include drinks, meat, sausage, bread, biscuit, rice cake, chocolate, candies, snacks, confectionery, pizza, ramen, other noodles, gums, dairy products including ice creams, various soups, beverages, alcoholic beverages, vitamin complexes, etc. and all health foods in ordinary sense.

The one or more selected from an *Oldenlandia brachypoda* extract, a *Spergularia marina* extract, a *Disporum smilacinum* extract, a *Persicaria posumbu* extract and a *Geum aleppicum* extract of the present disclosure may be added to a food either alone or in together with other food ingredients, according to commonly employed methods. The mixing amount of the active ingredient may be determined appropriately depending on the purpose of use (prevention or improvement). In general, the extract may be added to a food in an amount of 0.01-50 wt % based on the total weight of the food. However, in case of long-term ingestion for improvement or maintenance of health or sanitation, the amount may be smaller than the above-described range. And, since it has no safety problem at all, the active ingredient may be used in a larger amount than the above-described range.

As the food composition according to the present disclosure, a health functional drink composition may contain, in addition to the one or more selected from an *Oldenlandia brachypoda* extract, a *Spergularia marina* extract, a *Disporum smilacinum* extract, a *Persicaria posumbu* extract and a *Geum aleppicum* extract as an essential ingredient, other ingredients without particular limitation. For example, it may contain various sweeteners or natural carbohydrates, etc. as additional ingredients as in common drinks. Examples of the natural carbohydrate may include monosaccharides, e.g., glucose, fructose, etc., disaccharides, e.g., maltose, sucrose, etc., polysaccharides, e.g., dextrin, cyclodextrin, etc. and commonly used sugars and sugar alcohols such as xylitol, sorbitol, erythritol, etc. The sweetener may be either a natural sweetener (thaumatin, stevia extract (e.g., levaudioside A, glycyrrhizin, etc.) or a synthetic sweetener (saccharin, aspartame, etc.).

The food composition of the present disclosure containing the one or more selected from an *Oldenlandia brachypoda* extract, a *Spergularia marina* extract, a *Disporum smilacinum* extract, a *Persicaria posumbu* extract and a *Geum aleppicum* extract may contain various nutrients, vitamins, minerals (electrolytes), flavors including synthetic flavors and natural flavors, colorants, thickeners (cheese, chocolate, etc.), pectic acid and salts thereof, alginic acid and salts thereof, organic acids, protective colloidal thickeners, pH control agents, stabilizers, antiseptics, glycerin, alcohols, carbonating agents used in carbonated beverages, or the like.

The present disclosure also provides a method for suppressing appetite, preventing obesity, improving heart diseases, improving arteriosclerosis, preventing or improving diabetes, improving digestion and malabsorption, protecting nerves and/or treating or improving liver diseases, which includes administering a therapeutically effective amount or an amount for health improvement of the one or more selected from an *Oldenlandia brachypoda* extract, a *Spergularia marina* extract, a *Disporum smilacinum* extract, a *Persicaria posumbu* extract and a *Geum aleppicum* extract to a patient or an individual in need of treatment or improvement of conditions.

That is to say, the present disclosure provides a use of one or more selected from an *Oldenlandia brachypoda* extract, a *Spergularia marina* extract, a *Disporum smilacinum* extract, a *Persicaria posumbu* extract and a *Geum aleppicum* extract as a drug or a health functional food for suppressing appetite, preventing obesity, improving heart diseases, preventing or improving diabetes, improving digestion and malabsorption, improving arteriosclerosis, protecting nerves and/or treating or improving liver diseases.

Advantageous Effects

The present disclosure provides a use of one or more selected from an *Oldenlandia brachypoda* extract, a *Spergularia marina* extract, a *Disporum smilacinum* extract, a *Persicaria posumbu* extract and a *Geum aleppicum* extract for treating diabetes, suppressing appetite, preventing obesity, improving heart diseases, improving digestion and malabsorption, improving arteriosclerosis, protecting nerves and/or treating or Improving liver diseases. A pharmaceutical composition or a food composition according to the present disclosure exhibits few side effect and is safe because it uses the natural extract, and exhibits an excellent effect of treating diabetes, suppressing appetite, preventing obesity, improving heart diseases, improving digestion and malabsorption, improving arteriosclerosis, protecting nerves and/or treating or improving liver diseases.

EMBODIMENTS

Figure 1:
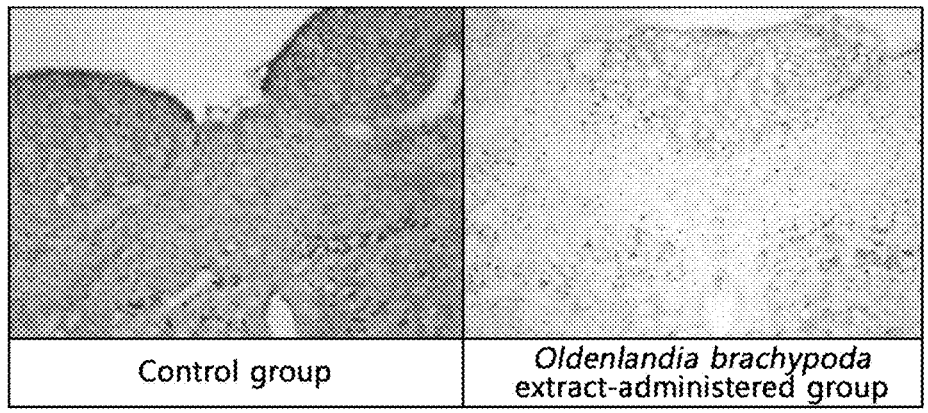
FIG. 1 shows activation of c-Fos in the caudal DVC (dorsal vagal complex) after administration of an *Oldenlandia brachypoda* extract.

Hereinafter, the present disclosure will be described in detail through examples. However, the following examples are for illustrative purposes only and it will be apparent to those of ordinary skill in the art that the scope of the present disclosure is not limited by the examples.

Example 1. Preparation of Extract

<1> Preparation of *Oldenlandia brachypoda* Extract

An 80% ethanol extract of *Oldenlandia brachypoda* was prepared using *Oldenlandia brachypoda* acquired from the Jeju Biodiversity Research Institute (JBRI-10170). Specifically, the whole plant of *Oldenlandia brachypoda* excluding the root was freeze-dried and ground. Then, after adding 50 mL of 80 wt % ethanol per 1 g of the sample, extraction was conducted at room temperature for 3 days. The resulting extract was filtered 2 times through filter paper (Whatman No. 1, England), concentrated using a rotary vacuum evaporator (B-480, Buchi, Switzerland), freeze-dried again and then powdered.

<2> Preparation of *Spergularia Marina* Extract and Fractions Thereof

Preparation of Extract

The whole plant of *Spergularia marina* excluding the root was purchased in Haenam, Jeollanam-do, Korea. First, the sample was freeze-dried and ground. Then, after adding 40 mL of 50 wt % ethanol per 1 g of the sample, extraction was conducted at room temperature for 3 days. The resulting extract was filtered 2 times through filter paper (Whatman No. 1, England), concentrated using a rotary vacuum evaporator (B-480, Buchi, Switzerland), freeze-dried again and then powdered.

Preparation of Fractions

The 50% ethanol extract was dissolved in water, sequentially fractionated using solvents which are less polar than water (hexane, ethyl acetate, chloroform and butanol) and then freeze-dried.

<3> Preparation of *Disporum smilacinum* Extract

The whole plant of *Disporum smilacinum* excluding the root was purchased in Hwasun, Jeollanam-do, Korea. First, the sample was freeze-dried and ground. Then, after adding 40 mL of 50 wt % ethanol per 1 g of the sample, extraction was conducted at room temperature for 3 days. The resulting extract was filtered 2 times through filter paper (Whatman No. 1, England), concentrated using a rotary vacuum evaporator (B-480, Buchi, Switzerland), freeze-dried again and then powdered.

<4> Preparation of *Persicaria posumbu* Extract

An 80% ethanol extract of *Persicaria posumbu* was prepared using *Persicaria posumbu* acquired from the Jeju Biodiversity Research Institute (JBRI-10714). Specifically, the whole plant of *Persicaria posumbu* excluding the root was freeze-dried and ground. Then, after adding 50 mL of 80 wt % ethanol per 1 g of the sample, extraction was conducted at room temperature for 3 days. The resulting extract was filtered 2 times through filter paper (Whatman No. 1, England), concentrated using a rotary vacuum evaporator (B-480, Buchi, Switzerland), freeze-dried again and then powdered.

<5> Preparation of *Geum aleppicum* Extract

An 80% ethanol extract of *Geum aleppicum* was prepared using *Geum aleppicum* acquired from the Jeju Biodiversity Research Institute (JBRI-10611). Specifically, the whole plant of *Geum aleppicum* excluding the root was freeze-dried and ground. Then, after adding 50 mL of 80 wt % ethanol per 1 g of the sample, extraction was conducted at room temperature for 3 days. The resulting extract was filtered 2 times through filter paper (Whatman No. 1, England), concentrated using a rotary vacuum evaporator (B-480, Buchi, Switzerland), freeze-dried again and then powdered.

Experiments were conducted as follows in order to investigate whether one or more of the *Oldenlandia brachypoda* extract, the *Spergularia marina* extract, the *Disporum smilacinum* extract, the *Persicaria posumbu* extract and the *Geum aleppicum* extract obtained as described above is effective in promoting the secretion of gut hormones or neuropeptides.

Example 2. Stimulation of GLP-1 Secretion and Activation of GPR119 in NCI-H716 Cells 1. Cell Culturing Human-derived NCI-H716 cells were purchased from the American Type Culture Collection (ATCC; Manassas, Va.). The cells were cultured in RPMI 1640 medium containing 10% fetal bovine serum (FBS), 2 mM L-glutamine, 100 IU/mL penicillin and 100 µg/mL streptomycin.

2. Measurement of GLP-1 Secretion from Sample

The NCI-H716 cells were cultured on a 96-well plate for 3 days to a concentration of $2 \times 10^5$ cells/mL. On the day of the experiment, the cells were washed with phosphate-buffered saline (PBS) and incubated at 37° C. for 1 hour in Krebs-Ringer bicarbonate buffer (KRB, 128.8 mmol/L NaCl, 4.8 mmol/L KCl, 1.2 mmol/L $KH_2PO_4$, 1.2 mmol/L $MgSO_4$, 2.5 mmol/L $CaCl_2$, 5 mmol/L $NaHCO_3$, 10 mmol/L HEPES, 0.2% BSA, pH 7.4) to which the sample was added. Then, for GLP-1 assay, the supernatant (100 µL) was taken and analyzed using an active GLP-1 ELISA kit (EGLP-35K, Millipore). The concentration of GLP-1 was calculated GLP-1 standard (pmol/mL) and the result was expressed as fold of control by comparing the concentration of GLP-1 secreted by stimulation with the sample and the concentration of GLP-1 secreted by stimulation with a control substance.

3. Measurement of Change in Intracellular Level of Calcium

The change in intracellular level of calcium was measured by a fluorescence-based assay. After plating the cells onto a 96-well plate at a concentration of $4.0 \times 10^4$ cells/well, the intracellular $Ca^{2+}$ concentration was measured 48 hours using the Calcium 5 assay kit (Molecular Devices) and the fluorometric imaging plate reader (FLIPR™) Flexstation III (Molecular Devices Co., Sunnyvale, Calif., USA). After sample injection, fluorescence from stained calcium was measured for 120 seconds at wavelengths of 488 nm (excitation) and 525 (emission). The result was calculated automatically as maximum fluorescent value−minimum fluorescent value=delta relative fluorescent units ($\Delta$RFU).

When GPCRs are activated by specific substances, the G protein complexes (G$\alpha$-gustducin, G$\alpha$-transtducin, G$\alpha$14, G$\beta$3, G$\beta$1, G$\gamma$13) coupled with the GPCRs are activated. This leads to activation of phospholipases ant thus activation of type III IP3-receptors, resulting in the increase of $Ca^{2+}$ concentration in the cytoplasm. Accordingly, it was expected that the activation of GPCRs can be measured by monitoring the change in the intracellular level of $Ca^{2+}$ ion.

Also, since the activation of TRP channels leads to influx of calcium ions from outside the cell membrane into the cells, it was expected that the activation of the TRP channels can be measured by monitoring the change in the intracellular level of $Ca^{2+}$ ion.

4. Measurement of cAMP

The NCI-H716 cells were plated onto a 24-well culture plate at a concentration of $1 \times 10^6$ cells/mL and cultured for 3 days. On the day of the experiment, the cells were incubated with the sample in KRB buffer at 37° C. using a 5% $CO_2$ incubator. After the incubation, the medium was removed and the cells were washed 3 times with KRB buffer. They were then incubated at 150 rpm at room temperature for 20 minutes after adding 0.5 mL of 0.1 N HCl. The incubated cells were then centrifuged at 1000 g for 10 minutes and the supernatant was analyzed by an enzyme immunoassay (EIA) using the cyclic AMP kit.

5. Gene Knockdown by siRNA Transfection siRNA sequence targeting human α-gustducin (GNAT3, accession no. NM 001102386, Dharmacon on-target SMARTpool siRNA reagent), GPR119 (taste receptor, type 2, member 38/GeneBank accession no. NM_176817) and non-target SMARTpool siRNA were purchased from Dharmacon (Lafayette, Colo.). The NCI-H716 cells were transfected with the siRNAs for 48 hours using the Neon™ transfection system (Invitrogen, Carlsbad, Calif.). Then, GLP-1 secretion and the concentrations of $Ca^{2+}$ and cAMP were measured.

6. Result

The concentrations of GLP-1 and cAMP were measured by the EIA. The change in the intracellular level of calcium was expressed as relative fluorescent units (ΔRFU). The experiments were carried out in triplicate and repeated 3 times, and the result was represented as mean±S.E.M (n=9). *$p<0.05$; $p<0.01$; $p<0.001$ vs. control.

<1> Oldenlandia brachypoda Extract 2-1-1. Effect of Oldenlandia brachypoda 80% Ethanol Extract on GLP-1 Secretion in NCI-H716 Cells

TABLE 1

| Sample | Concentration | GLP-1 (fold of control) |
|---|---|---|
| Control | | 1.000 ± 0.088 |
| Oldenlandia brachypoda (80% ethanol extract) | 100 µg/mL | 1.370 ± 0.177* |
| | 250 µg/mL | 2.714 ± 0.109* |
| | 500 µg/mL | 3.530 ± 0.156* |

As seen from Table 1, Oldenlandia brachypoda (80% ethanol extract) had an effect of promoting GLP-1 secretion in the NCI-H716 cells in a concentration-dependent manner. Accordingly, it is expected that Oldenlandia brachypoda (80% ethanol extract) can exhibit, by promoting GLP-1 secretion from enteroendocrine cells, an effect of treating diabetes through glucose-dependent stimulation of insulin secretion, increase of insulin gene expression, promotion of proliferation of pancreatic beta cells, enhancement of survival of pancreatic beta cells, suppression of glucagon secretion, decrease of blood sugar level, etc. in the pancreas.

Also, it is expected that it can exhibit an effect of treating obesity by slowing the gastric emptying rate, suppressing appetite, increasing satiety and suppressing food intake, exhibit an effect of treating heart diseases by protecting cardiomyocytes from ischemia and improving the heart functions of a patient with a concern of heart failure, and allow for effective control of digestion and absorption by increasing the secretion of digestive enzymes in the pancreas and the small intestine.

Accordingly, it is expected that the extract can exhibit an effect of treating neurodegenerative diseases, cerebrovascular diseases and neuroinflammation and promoting neurogenesis.

Also, it is expected that it can exhibit an effect of improving liver diseases by reducing hepatic inflammation, enhancing enterohepatic blood flow, improving hepatic functions, treating cholestatic liver diseases, treating pruritus and painless jaundice, improving intestinal functions and promoting neurotransmission.

In addition, it is expected that the extract will be useful in improving arteriosclerosis.

2-1-2. Change in Intracellular $Ca^{2+}$ Concentration in NCI-H716 Cells by Oldenlandia brachypoda 80% Ethanol Extract

TABLE 2

| Sample | Concentration | Change in $Ca^{2+}$ (ΔRFU) |
|---|---|---|
| Control | | 9.181 ± 0.632 |
| Oldenlandia brachypoda (80% ethanol extract) | 100 µg/mL | 24.661 ± 3.631* |
| | 250 µg/mL | 39.087 ± 5.531** |
| | 500 µg/mL | 55.187 ± 3.800*** |

As seen from Table 2, the 100, 250 and 500 µg/mL Oldenlandia brachypoda 80% ethanol extracts significantly increased the intracellular level of calcium as compared to the control group. It is thought that the Oldenlandia brachypoda 80% ethanol extract increased the GLP-1 secretion by increasing the intracellular calcium concentration.

Accordingly, it is expected that the Oldenlandia brachypoda extract of the present disclosure can exhibit, by increasing the GLP-1 secretion by increasing the intracellular level of calcium, an effect of treating diabetes through promotion of insulin secretion in pancreatic beta cells, increase of Insulin gene expression, suppression of glucagon secretion, decrease of blood sugar level, etc.

In addition, it is expected that the Oldenlandia brachypoda extract can exhibit an effect of improving digestion and malabsorption by regulating intestinal contraction and motility and exhibit an effect of protecting cardiomyocytes by controlling bloodstream to the cardiac muscle.

2-1-3. Increase of Intracellular cAMP in NCI-H716 Cells by Oldenlandia brachypoda 80% Ethanol Extract

TABLE 3

| Sample | Concentration | cAMP (fold of control) |
|---|---|---|
| Control | | 1.000 ± 0.100 |
| Oldenlandia brachypoda (80% ethanol extract) | 500 µg/mL | 65.174 ± 12.943*** |
| OEA (oleoylethanolamide) | 20 µM | 6.813 ± 1.634* |

As seen from Table 3, Oldenlandia brachypoda (80% ethanol extract) exhibited the effect of increasing intracellular cAMP as compared to the control group. It is thought that the Oldenlandia brachypoda extract can increase the secretion of GLP-1 by increasing the level of cAMP which is one of the signaling molecules of GPCRs.

Accordingly, it is expected that the Oldenlandia brachypoda extract of the present disclosure can exhibit, by increasing the GLP-1 secretion by increasing the intracellular cAMP concentration, an effect of treating diabetes through promotion of insulin secretion in pancreatic beta cells, increase of insulin gene expression, suppression of glucagon secretion, decrease of blood sugar level, etc. Also, it is expected that it can exhibit an effect of preventing obesity by suppressing appetite and Increasing satiety.

In addition, it is expected that the Oldenlandia brachypoda extract can exhibit an effect of improving digestion and malabsorption by regulating intestinal contraction and motility and exhibit an effect of protecting cardiomyocytes by controlling bloodstream to the cardiac muscle.

<2> *Spergularia marina* Extract 2-1. Effect of *Spergularia marina* 50% Ethanol Extract on GLP-1 Secretion in NCI-H716 Cells

TABLE 4

| Sample | Concentration | GLP-1 secretion (fold of control) |
|---|---|---|
| Control |  | 1.000 ± 0.162 |
| *Spergularia marina* (50% ethanol extract) | 100 μg/mL | 1.616 ± 0.221* |
|  | 250 μg/mL | 5.480 ± 0.312*** |
|  | 500 μg/mL | 7.337 ± 0.431*** |

As seen from Table 4, *Spergularia marina* (50% ethanol extract) had an effect of promoting GLP-1 secretion in the NCI-H716 cells in a concentration-dependent manner.

Accordingly, it is expected that the extract can exhibit an effect of treating neurodegenerative diseases, cerebrovascular diseases and neuroinflammation and promoting neurogenesis.

Also, it is expected that it can exhibit an effect of improving liver diseases by reducing hepatic inflammation, enhancing enterohepatic blood flow, improving hepatic functions, treating cholestatic liver diseases, treating pruritus and painless jaundice, improving intestinal functions and promoting neurotransmission.

In addition, it is expected that the extract will be useful in improving arteriosclerosis.

2-2-2. Change in Intracellular $Ca^{2+}$ Concentration in NCI-H716 Cells by *Spergularia marina* 50% Ethano Extract

TABLE 5

| Sample | Concentration | Change in $Ca^{2+}$ concentration (ΔRFU) |
|---|---|---|
| Control |  | 6.491 ± 0.133 |
| *Spergularia marina* (50% ethanol extract) | 100 μg/mL | 14.453 ± 2.606* |
|  | 250 μg/mL | 19.791 ± 2.148** |
|  | 500 μg/mL | 25.701 ± 2.233** |

As seen from Table 5, the 100, 250 and 500 μg/mL *Spergularia marina* 50% ethanol extracts significantly increased the intracellular level of calcium as compared to the control group. It is thought that the increased intracellular calcium concentration is caused by the increased movement of calcium ions due to the activation of GPCRs. Accordingly, it is expected that the *Spergularia marina* extract will increase GLP-1 secretion and be effective for preventing obesity by activating GPCRs.

2-2-3. Increase of Intracellular cAMP in NCI-H716 Cells by *Spergularia marina* 50% Ethanol Extract

TABLE 6

| Sample | Concentration | cAMP (fold of control) |
|---|---|---|
| Control |  | 1.000 ± 0.192 |
| *Spergularia marina* (50% ethanol extract) | 500 μg/mL | 9.986 ± 2.224*** |
| OEA (oleoylethanolamide) | 20 μM | 6.813 ± 1.634* |

As seen from Table 6, *Spergularia marina* (50% ethanol extract) exhibited the effect of Increasing intracellular cAMP as compared to the control group. It is thought that the *Spergularia marina* extract can increase the secretion of GLP-1 by increasing the level of cAMP which is one of the signaling molecules of GPCRs. Accordingly, it is expected that the *Spergularia marina* extract can exhibit an effect of preventing obesity, suppressing appetite, improving heart diseases, improving digestive disorders and improving malabsorption.

2-2-4 Effect of 5 Fractions of *Spergularia marina* 50% Ethanol Extract on GLP-1 Secretion in NCI-H716 Cells

TABLE 7

| Concentration | Fraction | GLP-1 secretion (fold of control) |
|---|---|---|
| 500 μg/mL | Control | 1.000 ± 0.068 |
|  | *Spergularia marina* (50% ethanol extract) | 7.337 ± 0.431*** |
|  | Hexane layer | 8.712 ± 0.246 *** |
|  | Chloroform layer | 11.575 ± 0.222 *** |
|  | Ethyl acetate layer | 4.650 ± 0.558 * |
|  | Butanol layer | 6.334 ± 0.875 ** |
|  | $H_2O$ layer | 4.395 ± 0.671 * |

As seen from Table 7, the hexane fraction and the chloroform fraction of *Spergularia marina* exhibit better effect of increasing GLP-1 secretion than the *Spergularia marina* extract (50% ethanol extract).

Accordingly, it can be expected that the extract can exhibit an effect of treating neurodegenerative diseases, cerebrovascular diseases and neuroinflammation and promoting neurogenesis.

Also, it is expected that it can exhibit an effect of improving liver diseases by reducing hepatic inflammation, enhancing enterohepatic blood flow, improving hepatic functions, treating cholestatic liver diseases, treating pruritus and painless jaundice, improving intestinal functions and promoting neurotransmission.

In addition, it is expected that the extract will be useful in improving arteriosclerosis.

2-2-5. Effect of *Spergularia marina* on GLP-1 in NCI-H716 Cells Treated with α-Gustducin siRNA

TABLE 8

| | | GLP-1 secretion (fold of control) | | |
|---|---|---|---|---|
| Sample | Concentration | Control siRNA | α-Gustducin siRNA | Inhibition (%) |
| Control |  | 1.000 ± 0.108 | 1.000 ± 0.197 | 0 |
| *Spergularia marina* (50% ethanol extract) | 100 μg/mL | 1.248 ± 0.304 | 0.301 ± 0.084* | 75.85 |
|  | 250 μg/mL | 3.739 ± 1.159 | 0.460 ± 0.110** | 87.69 |
|  | 500 μg/mL | 5.994 ± 0.323 | 3.338 ± 0.220** | 44.31 |
| Glucose | 500 mM | 6.386 ± 0.327 | 1.363 ± 0.320*** | 78.65 |

±S.E.M (n = 9); *p < 0.05; p < 0.01; *P < 0.001 vs. control siRNA.

The transfection of the cells with α-gustducin-targeted siRNA leads to knockdown of the α-gustducin gene. Since the effect of increasing GLP-1 secretion of the *Spergularia marina* 50% ethanol extract was significantly inhibited under this condition, it was confirmed that the *Spergularia marina* 50% ethanol extract acts as an α-gustducin agonist.

2-2-6. Effect of *Spergularia Marina* on GLP-1 in NCI-H716 Cells Treated with GPR119 siRNA

TABLE 9

| Sample | Concentration | GLP-1 secretion (fold of control) | | Inhibition (%) |
|---|---|---|---|---|
| | | Control siRNA | GPR119 siRNA | |
| Control | | 1.000 ± 0.062 | 1.033 ± 0.054 | |
| *Spergularia marina* (50% ethanol extract) | 10 µg/mL | 2.840 ± 0.082 | 1.354 ± 0.235 | |
| | 50 µg/mL | 3.098 ± 0.022 | 1.681 ± 0.567 | |
| | 100 µg/mL | 3.829 ± 0.278 | 2.094 ± 0.172 | |
| | 250 µg/mL | 4.401 ± 0.107 | 2.559 ± 0.303** | 41.853 |
| | 500 µg/mL | 4.767 ± 0.307 | 2.948 ± 0.216** | 38.152 |
| OEA (oleoylethanolamide) | 20 µM | 4.822 ± 0.358 | 2.975 ± 0.241** | 38.303 |

±S.E.M (n = 9); *p < 0.05; p < 0.01; *P < 0.001 vs. control siRNA.

The transfection of the cells with GPR119 siRNA leads to knockdown of the GPR119 gene. Since the effect of Increasing GLP-1 secretion of the *Spergularia marina* 50% ethanol extract was significantly inhibited under this condition, it was confirmed that the *Spergularia marina* 50% ethanol extract acts as a GPR119 agonist.

Since GPR119 is a signaling molecule is involved also in cAMP production, the effect on cAMP production was also investigated.

2-2-7. Effect of *Spergularia marina* on Intracellular cAMP in NCI-H716 Cells Treated with GPR119 siRNA

TABLE 10

| Sample | Conc. (µg/mL) | cAMP (fold of control) | | Inhibition (%) |
|---|---|---|---|---|
| | | Control siRNA | GPR119 siRNA | |
| Control | | 1.000 ± 0.192 | 1.466 ± 0.178 | |
| *Spergularia marina* (50% ethanol extract) | 250 µg/mL | 3.046 ± 0.865 | 2.331 ± 0.466* | 23.473 |
| | 500 µg/mL | 9.986 ± 2.224 | 5.182 ± 0.641* | 48.101 |

±S.E.M (n = 9); *p < 0.05; p < 0.01; *P < 0.001 vs. control siRNA.

The transfection of the cells with GPR119 siRNA leads to knockdown of the GPR119 gene. Since the effect of Increasing GLP-1 secretion of the *Spergularia marina* 50% ethanol extract was significantly inhibited under this condition as seen from Table 10, it was confirmed that the *Spergularia marina* 50% ethanol extract acts as a GPR119 agonist.

<3> *Disporum smilacinum* Extract 2-3-1. Effect of *Disporum smilacinum* 50% Ethanol Extract on GLP-1 Secretion in NCI-H716 Cells

TABLE 11

| Sample | Concentration | GLP-1 secretion (fold of control) |
|---|---|---|
| Control | | 1.000 ± 088 |
| *Disporum smilacinum* (50% ethanol extract) | 100 µg/mL | 1.502 ± 0.0802* |
| | 250 µg/mL | 1.956 ± 0.0495* |
| | 500 µg/mL | 3.145 ± 0.338** |
| Glucose | 100 mM | 2.694 ± 0.024* |

As seen from Table 11, *Disporum smilacinum* (50% ethanol extract) had an effect of promoting GLP-1 secretion in the NCI-H716 cells in a concentration-dependent manner.

2-3-2. Change in Intracellular $Ca^{2+}$ Concentration in NCI-H716 Cells by *Disporum smilacinum* 50% Ethanol Extract

TABLE 12

| Sample | Concentration | Change in $Ca^{2+}$ concentration (ΔRFU) |
|---|---|---|
| Control | | 9.181 ± 632 |
| *Disporum smilacinum* (50% ethanol extract) | 100 µg/mL | 23.132 ± 0.724*** |
| | 250 µg/mL | 26.959 ± 0.161*** |
| | 500 µg/mL | 31.062 ± 4.084** |
| Glucose | 100 mM | 10.240 ± 0.352** |

As seen from Table 12, the 100, 250 and 500 µg/mL *Disporum smilacinum* 50% ethanol extracts significantly increased the intracellular level of calcium as compared to the control group. It is thought that the increased intracellular calcium concentration is caused by the increased movement of calcium ions due to the activation of GPCRs. Accordingly, it is expected that the *Disporum smilacinum* extract will increase GLP-1 secretion and be effective for preventing and treating diabetes, improving heart disease, suppressing appetite and preventing obesity by activating GPCRs and thereby increasing GLP-1 secretion.

It is also expected that the extract can exhibit an effect of treating neurodegenerative diseases, cerebrovascular diseases and neuroinflammation and promoting neurogenesis.

Also, it is expected that it can exhibit an effect of improving liver diseases by reducing hepatic inflammation, enhancing enterohepatic blood flow, improving hepatic functions, treating cholestatic liver diseases, treating pruritus and painless jaundice, improving intestinal functions and promoting neurotransmission.

In addition, it is expected that the extract will be useful in improving arteriosclerosis.

2-3-3. Increase of intracellular cAMP in NCI-H716 cells by *Disporum smilacinum* 50% ethanol extract

TABLE 13

| Sample | Concentration | cAMP (fold of control) |
|---|---|---|
| Control | | 1.000 ± 0.100 |
| *Disporum smilacinum* (50% ethanol extract) | 500 µg/mL | 10.203 ± 0.612* |
| OEA (oleoylethanolamide) | 20 µM | 6.813 ± 1.634* |

As seen from Table 13, *Disporum smilacinum* (50% ethanol extract) exhibited the effect of increasing intracellular cAMP as compared to the control group. It is thought that the *Disporum smilacinum* extract can increase the secretion of GLP-1 by increasing the level of cAMP which is closely related with the calcium level. Accordingly, it is expected that the *Disporum smilacinum* extract can exhibit an effect of treating obesity by suppressing appetite and increasing satiety. Also, it is expected that it can exhibit an effect of improving heart diseases by protecting cardiomyocytes and exhibit an effect of treating diabetes by increasing insulin secretion.

<4> *Geum aleppicum* Extract 2-4-1. Effect of *Geum aleppicum* 80% Ethanol Extract on GLP-1 Secretion in NCI-H716 Cells

TABLE 14

| Sample | Concentration | GLP-1 secretion (fold of control) |
|---|---|---|
| Control | | 1.000 ± 0.088 |
| *Geum aleppicum* (80% ethanol extract) | 500 µg/mL | 2.396 ± 0.226* |

As seen from Table 14, *Geum aleppicum* (80% ethanol extract) had an effect of promoting GLP-1 secretion in the NCI-H716 cells. Accordingly, it is expected that *Geum aleppicum* (80% ethanol extract) can exhibit, by promoting GLP-1 secretion from enteroendocrine cells, an effect of treating diabetes through glucose-dependent stimulation of insulin secretion, increase of insulin gene expression, promotion of proliferation of pancreatic beta cells, enhancement of survival of pancreatic beta cells, suppression of glucagon secretion, decrease of blood sugar level, etc. in the pancreas.

Also, it is expected that it can exhibit an effect of treating obesity by slowing the gastric emptying rate, suppressing appetite, increasing satiety and suppressing food intake, exhibit an effect of treating heart diseases by protecting cardiomyocytes from ischemia and improving the heart functions of a patient with a concern of heart failure, and allow for effective control of digestion and absorption by increasing the secretion of digestive enzymes in the pancreas and the small intestine.

It is also expected that the extract can exhibit an effect of treating neurodegenerative diseases, cerebrovascular diseases and neuroinflammation and promoting neurogenesis.

Also, it is expected that it can exhibit an effect of improving liver diseases by reducing hepatic inflammation, enhancing enterohepatic blood flow, improving hepatic functions, treating cholestatic liver diseases, treating pruritus and painless jaundice, improving intestinal functions and promoting neurotransmission.

In addition, it is expected that the extract will be useful in improving arteriosclerosis.

2-4-2. Change in Intracellular $Ca^{2+}$ Concentration in NCI-H716 Cells by *Geum aleppicum* 80% Ethanol Extract

TABLE 15

| Sample | Concentration | Change in $Ca^{2+}$ concentration (ΔRFU) |
|---|---|---|
| Control | | 9.181 ± 0.632 |
| *Geum aleppicum* (80% ethanol extract) | 500 µg/mL | 35.003 ± 1.984** |
| Glucose | 100 mM | 10.240 ± 0.352** |

As seen from Table 15, the 500 µg/mL *Geum aleppicum* 80% ethanol extract significantly increased the intracellular level of calcium as compared to the control group. It is thought that the increased intracellular calcium concentration is caused by the increased movement of calcium ions due to the activation of GPCRs.

Accordingly, it is expected that the *Geum aleppicum* extract of the present disclosure can exhibit an effect of treating diabetes through increase of insulin gene expression, suppression of glucagon secretion, decrease of blood sugar level, etc. Also, it is expected that it can exhibit an effect of preventing obesity by suppressing appetite and increasing satiety.

In addition, it is expected that the *Geum aleppicum* extract can exhibit an effect of improving digestion and malabsorptlon by regulating intestinal contraction and motility and exhibit an effect of protecting cardiomyocytes by controlling bloodstream to the cardiac muscle.

2-4-3. Increase of Intracellular cAMP in NCI-H716 Cells by *Geum aleppicum* 80% Ethanol Extract

TABLE 16

| Sample | Concentration | cAMP (fold of control) |
|---|---|---|
| Control | | 1.000 ± 0.100 |
| *Geum aleppicum* (80% ethanol extract) | 500 µg/mL | 13.365 ± 3.321* |
| OEA (oleoylethanolamide) | 20 µM | 6.813 ± 1.634* |

As seen from Table 16, the *Geum aleppicum* 80% ethanol extract exhibited the effect of increasing intracellular cAMP as compared to the control group. It is thought that the *Geum aleppicum* extract can increase the secretion of GLP-1 by increasing the level of cAMP which is closely related with the calcium level. Accordingly, it is expected that the *Geum aleppicum* extract can exhibit an effect of treating obesity by suppressing appetite and increasing satiety. Also, it is expected that it can exhibit an effect of improving heart diseases by protecting cardiomyocytes and exhibit an effect of treating diabetes by increasing insulin secretion.

Example 3. Measurement of TGR5 Activity

1. Cell Culturing

CHO-K1 cells were acquired from the ATCC (Manassas, Va.) and cultured in Ham's F-12K medium containing 10% (v/v) fetal bovine serum (FBS), 100 U/mL penicillin and 100 µg/mL streptomycin.

2. Measurement of TGR5 Activity

G-protein-coupled bile add receptor 1 [*Homo sapiens*] (GPBAR1, TGR5) as hTGR5 plasmid DNA and transcript variant 3 as transfection-ready DNA were purchased from OriGene. A 4.5-Kb pCMV6-XL5 vector with 1.4-Kb GPBAR1 (TGR5) inserted was used. After multiplication in transformed *E. coli* containing 100 µg/mL ampicillin, a TGR5 plasmid was obtain using the Invitrogen Purelink (high pure filter maxiprep) kit. The TGR5-expressing plasmid (pCMV6-XL5/TGR5), 400 ng/well, was transfected into the CHO-K1 cells together with a CRE-driven luciferase reporter plasmid, 100 ng/well, using Neon™ (Invitrogen, Cergy Pontoise, France). 48 hours later, after incubation with the sample for 5 hours, luciferase activity was measured using the Dual-Glo™ luciferase assay kit (Promega). Luminescence was measured using Victor3™ (PerkinElmer).

3. Result

<1> *Oldenlandia brachypoda* Extract 3-1-1. Increase of TGR5 Activity in CHO-K1 Cells Transfected with hTGR5 by *Oldenlandia brachypoda* 80% Ethanol Extract The CHO-K1 cells transfected with the TGR5 plasmid were treated with the *Oldenlandia brachypoda* 80% ethanol extract for 5 hours. TGR5 activity was evaluated by measuring the luciferase activity as described above. All the measurement data were expressed as mean±SEM. n=9. *p<0.05, **p<0.001 vs. control.

TABLE 17

| Sample | Concentration | TGR5 activity (fold of control) |
| --- | --- | --- |
| Control | | 1.000 ± 0.120 |
| *Oldenlandia brachypoda* (80% ethanol extract) | 100 µg/mL | 4.721 ± 0.553*** |
| Lithocholic acid (LCA) | 5 µM | 3.483 ± 0.119*** |

As seen from Table 17, the TGR5 activity was increased in the hTGR5-transfected cells by the *Oldenlandia brachypoda* 80% ethanol extract. Accordingly, it is expected that the *Oldenlandia brachypoda* extract can exhibit, by activating hTGR5 expressed in enteroendocrine cells and thereby increasing intracellular cAMP concentration and increasing GLP-1 secretion, an effect of treating diabetes through promotion of proliferation of pancreatic beta cells, increase of insulin gene expression, suppression of glucagon secretion, decrease of blood sugar level, etc. Also, it is expected that it can exhibit an effect of preventing obesity by suppressing appetite and increasing satiety.

It is also expected that the *Oldenlandia brachypoda* extract can exhibit an effect of improving digestion and malabsorption by regulating intestinal contraction and motility and exhibit an effect of protecting cardiomyocytes by controlling bloodstream to the cardiac muscle.

It is also expected that the extract can exhibit an effect of treating neurodegenerative diseases, cerebrovascular diseases and neuroinflammation and promoting neurogenesis.

Also, it is expected that it can exhibit an effect of improving liver diseases by reducing hepatic inflammation, enhancing enterohepatic blood flow, improving hepatic functions, treating cholestatic liver diseases, treating pruritus and painless jaundice, improving intestinal functions and promoting neurotransmission.

In addition, it is expected that the extract will be useful in improving arteriosclerosis.

<2> *Spergularia marina* Extract 3-2-1. Increase of TGR5 Activity in CHO-K1 Cells Transfected with hTGR5 by *Spergularia marina* 50% Ethanol Extract

TABLE 18

| Sample | Concentration | TGR5 activity (fold of control) |
| --- | --- | --- |
| Control | | 1.000 ± 0.120 |
| *Spergularia marina* (50% ethanol extract) | 10 µg/mL | 2.034 ± 0.063*** |
| | 50 µg/mL | 2.910 ± 0.503* |
| | 100 µg/mL | 2.411 ± 0.112*** |

The CHO-K1 cells transfected with the TGR5 plasmid were treated with the *Spergularia marina* 50% ethanol extract for 5 hours. TGR5 activity was evaluated by measuring the luciferase activity as described above. All the measurement data were expressed as mean±SEM. n=9. *p<0.05, ***p<0.001 vs. control.

As seen from Table 18, the TGR5 activity was increased in the hTGR5-transfected cells by the *Spergularia marina* 50% ethanol extract. Accordingly, since the activation of TGR5 leads to an effect of treating obesity by increasing energy consumption, it is expected that the *Spergularia marina* extract can exhibit an effect of preventing obesity, suppressing appetite, improving heart diseases, improving digestive disorders and Improving malabsorption.

It is also expected that the extract can exhibit an effect of treating neurodegenerative diseases, cerebrovascular diseases and neuroinflammation and promoting neurogenesis.

Also, it is expected that it can exhibit an effect of improving liver diseases by reducing hepatic inflammation, enhancing enterohepatic blood flow, improving hepatic functions, treating cholestatic liver diseases, treating pruritus and painless jaundice, improving intestinal functions and promoting neurotransmission.

In addition, it is expected that the extract will be useful in improving arteriosclerosis.

3-2-2. Effect of 5 Fractions of *Spergularia marina* 50% Ethanol Extract on TGR5 Activity in CHO-K1 Cells The CHO-K1 cells transfected with the TGR5 plasmid (as control) were treated with the *Spergularia marina* 50% ethanol extract for 5 hours. TGR5 activity was evaluated by measuring the luciferase activity as described above. All the measurement data were expressed as mean±SEM. n=9. *p<0.05, ***p<0.001 vs. control.

TABLE 19

| Sample | Concentration | Fraction | TGR5 activity (fold of control) |
| --- | --- | --- | --- |
| Control | | | 1.000 ± 0.024 |
| *Spergularia marina* (50% ethanol extract) | 500 µg/mL | Before fractionation | 2.759 ± 0.303** |
| | 500 µg/mL | Hexane layer | 1.529 ± 0.012 |
| | 500 µg/mL | Chloroform layer | 1.689 ± 0.062 |
| | 500 µg/mL | Ethyl acetate layer | 3.279 ± 0.151*** |
| | 500 µg/mL | Butanol layer | 2.584 ± 0.448* |
| | 500 µg/mL | H$_2$O layer | 3.184 ± 0.512* |

As seen from Table 19, the ethyl acetate fraction showed better TGR5 activity than the *Spergularia marina* extract (50% ethanol extract). Accordingly, it is expected that the ethyl acetate fraction of the *Spergularia marina* extract will exhibits an effect of preventing obesity, suppressing appetite, improving heart diseases, improving digestive disorders and improving malabsorption.

<3> *Disporum smilacinum* Extract 3-3-1. Increase of TGR5 Activity in CHO-K1 Cells by *Disporum smilacinum* 50% Ethanol Extract The CHO-K1 cells transfected with the TGR5 plasmid were treated with the *Disporum smilacinum* 50% ethanol extract for 5 hours. TGR5 activity was evaluated by measuring the luciferase activity as described above. All the measurement data were expressed as mean±SEM. n=9. *p<0.05, ***p<0.001 vs. control.

TABLE 20

| Sample | Concentration | TGR5 activity (fold of control) |
|---|---|---|
| Control | | 1.000 ± 0.120 |
| *Disporum smilacinum* (50% ethanol extract) | 10 µg/mL | 1.900 ± 0.275* |
| | 50 µg/mL | 2.389 ± 0.540* |
| | 100 µg/mL | 3.741 ± 0.214** |
| Lithocholic acid (LCA) | 5 µM | 3.483 ± 0.119*** |

As seen from Table 20, the TGR5 activity was increased in the hTGR5-transfected cells by the *Disporum smilacinum* 50% ethanol extract. Accordingly, since the activation of TGR5 leads to, by promoting GLP-1 secretion, an effect of treating diabetes, treating heart diseases, suppressing appetite and preventing obesity, it is expected that the *Disporum smilacinum* extract can exhibit an effect of treating obesity by suppressing appetite, increasing satiety, etc. by increasing GLP-1 secretion through the activation of TGR5. It is also expected that it can exhibit an effect of improving heart diseases by protecting cardiomyocytes and exhibit an effect of treating diabetes by increasing insulin secretion.

It is also expected that the extract can exhibit an effect of treating neurodegenerative diseases, cerebrovascular diseases and neuroinflammation and promoting neurogenesis.

Also, it is expected that it can exhibit an effect of improving liver diseases by reducing hepatic inflammation, enhancing enterohepatic blood flow, improving hepatic functions, treating cholestatic liver diseases, treating pruritus and painless jaundice, improving intestinal functions and promoting neurotransmission.

In addition, it is expected that the extract will be useful in improving arteriosclerosis.

<4> *Geum aleppicum* Extract 3-4-1. Increase of TGR5 Activity in CHO-K1 Cells Transfected with hTGR5 by *Geum aleppicum* 80% Ethanol Extract The CHO-K1 cells transfected with the TGR5 plasmid were treated with the *Geum aleppicum* 80% ethanol extract for 5 hours. TGR5 activity was evaluated by measuring the luciferase activity as described above. All the measurement data were expressed as mean±SEM, n=9. *p<0.05, ***p<0.001 vs. control.

TABLE 21

| Sample | Concentration | TGR5 activity (fold of control) |
|---|---|---|
| Control | | 1000 ± 0.120 |
| *Geum aleppicum* (80% ethanol extract) | 100 µg/mL | 2.012 ± 0.332* |
| Lithocholic acid (LCA) | 5 µM | 3.483 ± 0.119*** |

As seen from Table 21, the TGR5 activity was increased in the hTGR5-transfected cells by the *Geum aleppicum* 80% ethanol extract. Accordingly, it is expected that the *Geum aleppicum* extract can exhibit an effect of treating obesity by suppressing appetite, increasing satiety, etc. It is also expected that it can exhibit an effect of improving heart diseases by protecting cardiomyocytes and exhibit an effect of treating diabetes by increasing insulin secretion.

It is also expected that the *Geum aleppicum* extract can exhibit an effect of improving digestion and malabsorption by regulating intestinal contraction and motility.

It is also expected that the extract can exhibit an effect of treating neurodegenerative diseases, cerebrovascular diseases and neuroinflammation and promoting neurogenesis.

Also, it is expected that it can exhibit an effect of improving liver diseases by reducing hepatic inflammation, enhancing enterohepatic blood flow, improving hepatic functions, treating cholestatic liver diseases, treating pruritus and painless jaundice, improving intestinal functions and promoting neurotransmission.

In addition, it is expected that the extract will be useful in improving arteriosclerosis.

Example 4. CCK Secretion in STC-1 Cells

1. Cell Culturing

STC-1 cells were cultured in Dulbecco's modified Eagle's medium (DMEM) containing 10% fetal bovine serum (FBS) and 1% penicillin-streptomycin in an incubator maintained at 37° C. and 5% $CO_2$.

The fetal bovine serum (FBS), the penicillin-streptomycin and the Dulbecco's modified Eagle's medium (DMEM) used for the culturing were purchased from Gibco.

2. Measurement of CCK Secretion

The cultured cells were inoculated onto a 24-well plate at a concentration of $2 \times 10^5$ cells/well and incubated under the condition of 37° C. and 5% $CO_2$. 72 hours later, the cells were washed 2 times with HEPES buffer (4.5 mM KCl, 1.2 mM $CaCl_2$, 1.2 mM $MgCl_2$, 10 mM glucose, 140 mM NaCl, 20 mM HEPES-Tris, pH 7.4) and then incubated at 37° C. for 60 minutes after adding the test substance to the HEPES buffer. After the incubation, the medium was centrifuged at 10000 rpm for 10 minutes and the resultant supernatant was stored at −70° C. for use in analysis. An enzyme immunoassay (EIA) kit (Phoenix Pharmaceuticals Inc., Belmont Calif.) was used.

3. Measurement of Change in Intracellular Calcium Level

The cells were inoculated onto a poly-D-Lysine-coated black 96-well clear-bottom plate (Thermo) at a concentration of $8.0 \times 10^4$ cells/well and incubated under the condition of 37° C. and 5% $CO_2$. 72 hours later, the cells were incubated at 37° C. for 60 minutes using the Calcium-5 assay kit (Molecular Devices) and the change in $Ca^{2+}$ level was measured using Flexstation III. The change in $Ca^{2+}$ level was monitored for about 120 seconds at fluorescence wavelengths of 488 nm (ex) and 525 nm (em) and for 2 seconds after injecting the compound for 20 seconds.

4. Result

<1> *Oldenlandia brachypoda* Extract 4-1-1. Effect of *Oldenlandia brachypoda* 80% Ethanol Extract on CCK Secretion in STC-1 Cells

TABLE 22

| Sample | Concentration | Fold of control (mean ± SEM) | t-test | p value |
|---|---|---|---|---|
| Control | | 1.00 ± 0.01 | | |
| *Oldenlandia brachypoda* 80% ethanol extract | 500 μg/mL | 9.70 ± 1.43 | ** | 0.004 |

Fold of control = sample value/untreated control value.
±S.E.M. (n = 9) ***p < 0.001 vs. control.

As seen from Table 22, the *Oldenlandia brachypoda* extract exhibited an effect of promoting CCK secretion in the STC-1 cells.

Accordingly, it is expected that the *Oldenlandia brachypoda* extract of the present disclosure can induce an antidiabetic effect by activating the CCK-A receptors of the vagus nerve fibers and thereby inhibiting glucose production and provide an anti-obesity effect by suppressing food intake.

Also, it is expected that it can exhibit an effect of treating indigestion by activating the regulation of the gastrointestinal feedback, promoting gastric emptying, regulating intestinal contraction and motility and promoting the external secretion of the pancreas.

4-1-2. Effect of *Oldenlandia brachypoda* 80% Ethanol Extract on Change in $Ca^{2+}$ Level in STC-1 Cells

TABLE 23

| Sample | Concentration | ΔRFU (mean ± S.E.M.) | t-test | p value |
|---|---|---|---|---|
| Control | 0.5% DMSO | 75.93 ± 4.26 | | |
| *Oldenlandia brachypoda* 80% ethanol extract | 500 μg/mL | 109.94 ± 7.09 | * | 0.015 |
| AITC | 0.1 mM | 105.41 ± 2.12 | ** | 0.003 |

±S.E.M. (n = 9) * p < 0.05,  p < 0.01, *p < 0.001 vs. control.

As seen from Table 23, the *Oldenlandia brachypoda* 80% ethanol extract significantly increased the intracellular level of calcium as compared to the control group. It is thought that the increase in the intracellular calcium concentration is related with increased CCK secretion.

Accordingly, it is expected that the *Oldenlandia brachypoda* extract of the present disclosure can induce an antidiabetic effect by activating the CCK-A receptors of the vagus nerve fibers and thereby inhibiting glucose production and provide an anti-obesity effect by suppressing food intake.

Also, it is expected that it can exhibit an effect of treating indigestion by activating the regulation of the gastrointestinal feedback, promoting gastric emptying, regulating intestinal contraction and motility and promoting the external secretion of the pancreas.

Accordingly, it is expected that the *Oldenlandia brachypoda* extract can exhibit, by secreting CCK from enteroendocrine cells and thereby activating hTGR5 expressed therein and by increasing intracellular cAMP concentration and thereby increasing GLP-1 secretion, an effect of treating diabetes through increase of insulin secretion in pancreatic beta cells, increase of insulin gene expression, suppression of glucagon secretion, decrease of blood sugar level, etc. Also, it is expected that it can exhibit an effect of preventing obesity by suppressing appetite and increasing satiety.

It is also expected that the *Oldenlandia brachypoda* extract can exhibit an effect of improving digestion and malabsorption by regulating intestinal contraction and motility and exhibit an effect of protecting cardiomyocytes and by controlling bloodstream to the cardiac muscle.

4-1-3. Effect of *Oldenlandia brachypoda* 80% Ethanol Extract on Membrane Potential Change in STC-1 Cells

TABLE 24

| Sample | Concentration | ΔRFU (mean ± SEM) | t-test | p value |
|---|---|---|---|---|
| Control | 0.5% DMSO | 59.12 ± 2.09 | | |
| *Oldenlandia brachypoda* 80% ethanol extract | 500 μg/mL | 146.03 ± 12.12 | *** | <0.001 |
| KCl | 0.1 mM | 17.01 ± 0.93 | *** | <0.001 |

±S.E.M. (n = 9) p < 0.01, * p < 0.001 vs. control.

As seen from Table 24, the *Oldenlandia brachypoda* 80% ethanol extract affected the membrane potential change. It is though that the activation of GPCRs led to the increased movement of Ions in the cells. Accordingly, it is expected that the *Oldenlandia brachypoda* extract can increase GLP-1 secretion by activating GPCRs.

Accordingly, it is expected that the *Oldenlandia brachypoda* extract of the present disclosure can exhibit an effect of treating diabetes through increase of insulin gene expression, suppression of glucagon secretion, decrease of blood sugar level, etc. Also, it is expected that it can exhibit an effect of preventing obesity by suppressing appetite and increasing satiety.

In addition, it is expected that the *Oldenlandia brachypoda* extract can exhibit an effect of improving digestion and malabsorption by regulating intestinal contraction and motility and exhibit an effect of protecting cardiomyocytes and by controlling bloodstream to the cardiac muscle.

<2> *Spergularia marina* Extract 4-2-1. Effect of *Spergularia marina* 50% Ethanol Extract on CCK Secretion in STC-1 Cells

TABLE 25

| Sample | Concentration | Fold of control (mean ± SEM) | t-test | p value |
|---|---|---|---|---|
| Control | 1% DMSO | 1.00 ± 0.01 | | |
| *Spergularia marina* 50% ethanol extract | 500 μg/mL | 12.72 ± 6.56 | *** | <0.001 |

Fold of control = sample value/untreated control value.
±S.E.M. (n = 9) *** p < 0.001 vs. control (1% DMSO).

As seen from Table 25, the *Spergularia marina* extract affected the activation of CCK secretion which is known to effectively regulate digestion and absorption, prevent obesity, etc.

4-2-2. Effect of 5 Fractions of *Spergularia marina* 50% Ethanol Extract on CCK Secretion in STC-1 Cells

TABLE 26

| Sample | Fraction | Concentration (μg/mL) | Fold of control (mean ± S.E.M.) | t-test | p value |
|---|---|---|---|---|---|
| Control | | | 1.00 ± 0.07 | | |
| *Spergularia marina* 50% ethanol extract | Before fractionation | 100 | 1.08 ± 0.12 | | |
| | Hexane layer | 100 | 100.75 ± 5.54 | *** | <0.001 |
| | Chloroform layer | 100 | 96.15 ± 4.57 | *** | <0.001 |
| | Ethyl acetate layer | 100 | 2.25 ± 0.88 | | 0.258 |
| | Butanol layer | 100 | 1.27 ± 0.07 | | 0.239 |
| | Distilled water layer | 100 | 1.18 ± 0.27 | | 0.752 |

Fold of control = sample value/untreated control value.
±S.E.M. (n = 9) *** $p < 0.001$ vs. before fractionation.

As seen from Table 26, the fractions of the *Spergularia marina* extract exhibited better effect of increasing CCK secretion than the extract itself.

4-2-3. Effect of 5 Fractions of *Spergularia marina* 50% Ethanol Extract of Different Concentrations on CCK Secretion in STC-1 Cells

TABLE 27

| Sample | Fraction | Concentration (μg/mL) | Fold of control (mean ± S.E.M.) | t-test | p value |
|---|---|---|---|---|---|
| Control | | | 1.00 ± 0.18 | | |
| *Spergularia marina* 50% ethanol extract | Before fractionation | 100 | 1.08 ± 0.31 | | |
| | Hexane layer | 10 | 2.55 ± 0.43 | * | 0.029 |
| | | 50 | 47.26 ± 0.75 | *** | <0.001 |
| | | 100 | 73.47 ± 3.63 | *** | <0.001 |
| | Chloroform layer | 10 | 1.00 ± 0.05 | | 0.559 |
| | | 50 | 31.85 ± 0.89 | *** | <0.001 |
| | | 100 | 61.92 ± 0.72 | *** | <0.001 |

Fold of control = sample value/untreated control value.
±S.E.M. (n = 9) * $p < 0.05$, *** $p < 0.001$ vs. before fractionation.

Table 27 shows the effect of the hexane fraction and the chloroform fraction, which showed the best effect of increasing CCK secretion from among the fractions of the *Spergularia marina* extract, at different concentrations. As seen from the table, the hexane fraction and the chloroform fraction increased CCK secretion in a concentration-dependent manner. In particular, the hexane fraction showed a better effect of increasing CCK secretion.

4-2-4. Effect of Inhibitor on Increase of CCK Secretion in STC-1 Cells by 5 Fractions of *Spergularia marina* 50% Ethanol Extract The STC-1 cells were pretreated for 30 minutes with 100 μM ruthenium red (RR) or with 50 μM HC-030031. After adding 50 μg/mL of the extract, the cells were incubated at 37° C. for 60 minutes.

TABLE 28

| Sample | Fraction | Inhibitor | Fold of control (mean ± S.E.M.) | t-test | p value | Inhibition (%) |
|---|---|---|---|---|---|---|
| Control | | | 1.00 ± 0.00 | | | |
| *Spergularia marina* 50% ethanol extract | Before fractionation | Untreated | 1.08 ± 0.08 | | | |
| | | RR | 0.38 ± 0.09 | | 0.118 | 44.26 |
| | | HC-030031 | 0.54 ± 0.06 | | 0.274 | 21.47 |
| | Hexane layer | Untreated | 36.87 ± 2.08 | | | |
| | | RR | 12.69 ± 0.66 | ** | 0.008 | 65.57 |
| | | HC-030031 | 12.88 ± 0.62 | ** | 0.008 | 65.06 |
| | Chloroform layer | Untreated | 13.41 ± 1.51 | | | |
| | | RR | 3.24 ± 0.78 | * | 0.027 | 75.81 |
| | | HC-030031 | 1.04 ± 0.28 | * | 0.015 | 92.28 |

Fold of control = sample value/untreated control value.
±S.E.M. (n = 9) * $p < 0.05$, ** $p < 0.01$ vs. untreated.

As seen from Table 28, treatment with the ruthenium red or HC-030031 which inhibit calcium release resulted in significant decrease in CCK secretion by the *Spergularia marina* 50% extract. Accordingly, it is expected that the fractions of the *Spergularia marina* extract act as CCK secretion activators.

<3> *Disporum smilacinum* Extract 4-3-1. Effect of *Disporum smilacinum* 50% Ethanol Extract on CC Secretion in STC-1 Cells

TABLE 29

| Sample | Concentration | Fold of control (mean ± SEM) | t-test | p value |
|---|---|---|---|---|
| Control | 1% DMSO | 1.00 ± 0.01 | | |
| *Disporum smilacinum* 50% ethanol extract | 100 µg/mL | 1.61 ± 0.23 | * | 0.043 |
| | 250 µg/mL | 1.92 + 0.22 | * | 0.036 |
| | 500 µg/mL | 3.91 ± 0.52 | ** | 0.006 |
| AITC | 0.1 mM | 21.57 ± 0.59 | *** | <0.001 |

Fold of control = sample value/untreated control value.
±S.E.M. (n = 9) *** p < 0.001 vs. control.

As seen from Table 29, the *Disporum smilacinum* extract affected the activation of CCK secretion.

4-3-2. Effect of *Disporum smilacinum* 50% Ethanol Extract on Change in $Ca^{2+}$ Level in STC-1 Cells

TABLE 30

| Sample | Concentration | ΔRFU (mean ± S.E.M.) | t-test | p value |
|---|---|---|---|---|
| Control | 0.5% DMSO | 75.93 ± 4.26 | | |
| *Disporum smilacinum* 50% ethanol extract | 100 µg/mL | 87.68 ± 2.84 | * | 0.05 |
| | 250 µg/mL | 93.58 ± 3.02 | * | 0.05 |
| | 500 µg/mL | 114.97 ± 9.20 | * | 0.018 |
| AITC | 0.1 mM | 105.41 ± 2.12 | ** | 0.003 |

±S.E.M. (n = 9) * p < 0.05,  p < 0.01, *p < 0.001 vs. control.

As seen from Table 30, the *Disporum smilacinum* 80% ethanol extract significantly increased the intracellular level of calcium as compared to the control group. It is thought that the increased intracellular calcium concentration is caused by the increased movement of calcium ions due to the activation of GPCRs. Accordingly, it is expected that the *Disporum smilacinum* extract can exhibit an effect of treating obesity by suppressing appetite, increasing satiety, etc., 4-3-3. Effect of *Disporum smilacinum* 50% Ethanol Extract on Membrane Potential Change in STC-1 Cells

TABLE 31

| Sample | Concentration | ΔRFU (mean ± SEM) | t-test | p value |
|---|---|---|---|---|
| Control | 0.5% DMSO | 59.12 ± 2.09 | | |
| *Disporum smilacinum* 50% ethanol extract | 500 µg/mL | 66.23 ± 0.77 | *** | <0.001 |
| KCl | 0.1 mM | 17.01 ± 0.93 | *** | <0.001 |

±S.E.M. (n = 9) p < 0.01, * p < 0.001 vs. control.

As seen from Table 31, the *Disporum smilacinum* 50% ethanol extract affected the membrane potential change. It is though that the activation of GPCRs led to the Increased movement of ions in the cells. Accordingly, it is expected that the *Disporum smilacinum* extract can increase GLP-1 secretion by activating GPCRs and can exhibit an effect of treating diabetes, improving heart diseases, suppressing appetite, preventing obesity, etc.

<4> *Persicaria posumbu* Extract

Effect on CCK Secretion 4-4-1. Effect of *Persicaria posumbu* 80% Ethanol Extract on CCK Secretion in STC-1 Cells

TABLE 32

| Sample | Concentration | Fold of control (mean ± S.E.M.) | t-test | p value |
|---|---|---|---|---|
| Control | 1% DMSO | 1.00 ± 0.01 | | |
| *Persicaria posumbu* 80% ethanol extract | 100 µg/mL | 12.30 ± 1.95 | ** | 0.004 |
| | 250 µg/mL | 41.35 ± 4.28 | *** | <0.001 |
| | 500 µg/mL | 65.06 ± 2.25 | *** | <0.001 |

Fold of control = sample value/untreated control value.
±S.E.M. (n = 9)  p < 0.01, * p < 0.001 vs. control.

As seen from Table 32, the *Persicaria posumbu* 80% extract affected the activation of CCK secretion in the STC-1 cells.

4-4-2. Effect of Inhibitor on Increase of CCK Secretion in STC-1 Cells by *Persicaria posumbu* 80% Ethanol Extract (1)

The STC-1 cells were pretreated for 30 minutes with 100 µM ruthenium red (RR) or with 50 µM HC-030031. After adding 500 µg/mL of the extract, the cells were incubated at 37° C. for 60 minutes.

TABLE 33

| Sample | Concentration | Inhibitor | Fold of control (mean ± S.E.M.) | t-test | p value | Inhibition (%) |
|---|---|---|---|---|---|---|
| Control | | | 1.00 ± 0.04 | | | |
| *Persicaria posumbu* 80% ethanol extract | 500 µg/mL | Untreated | 42.23 ± 4.03 | | | |
| | | RR | 22.00 ± 0.45 | ** | 0.008 | 47.89 |
| | | HC-030031 | 39.69 ± 1.24 | * | 0.05 | 6.00 |

±S.E.M. (n = 9)  p < 0.01, *p < 0.001 vs. control.

exhibit an effect of Improving heart diseases by protecting cardiomyocytes and exhibit an effect of treating diabetes by increasing insulin secretion.

As seen from Table 33, when the cells were incubated with the TRP antagonist RR or the TRPA1 antagonist HC-030031 together with the *Persicaria posumbu* 80% ethanol extract, the CCK secretion by the *Persicaria posumbu* 80% ethanol extract was inhibited by 47.89% and 6%, respectively. This suggests that the *Persicaria posumbu* 80% ethanol extract secretes CCK by acting as a TRP agonist or a TRPA1 agonist.

Accordingly, it is expected that the *Persicaria posumbu* extract of the present disclosure can exhibit an effect of treating diabetes through increase of insulin gene expression, suppression of glucagon secretion, decrease of blood sugar level, etc. Also, it is expected that it can exhibit an effect of preventing obesity by suppressing appetite and increasing satiety.

In addition, it is expected that the *Persicaria posumbu* extract can exhibit an effect of improving digestion and malabsorption by regulating intestinal contraction and motility.

4-4-3. Effect of Inhibitor on Increase of CCK Secretion in STC-1 Cells by *Persicaria posumbu* 80% Ethanol Extract (2)

The STC-1 cells were pretreated for 30 minutes with 400 µM TPPO or with 20 µM U-73122.

After adding 500 µg/mL of the extract, the cells were incubated at 37° C. for 60 minutes.

TABLE 34

| Sample | Concentration | Inhibitor | Fold of control (mean ± S.E.M.) | t-test | p value | Inhibition (%) |
|---|---|---|---|---|---|---|
| Control | 1% DMSO | | 1.00 ± 0.07 | | | |
| *Persicaria posumbu* 80% ethanol extract | 500 µg/mL | Untreated | 20.02 ± 0.94 | | | |
| | | TPPO | 14.14 ± 0.67 | ** | 0.007 | 29.36 |
| | | U-73122 | 14.07 ± 0.24 | ** | 0.004 | 29.72 |

Fold of control = sample value/untreated control value.
±S.E.M. (n = 9)  $p < 0.01$, * $p < 0.001$ vs. untreated.

As seen from Table 34, when the cells were incubated with the G protein inhibitor TPPO or the PLCβ2 Inhibitor U-73122 together with the *Persicaria posumbu* 80% ethanol extract, the CCK secretion by the *Persicaria posumbu* 80% ethanol extract was inhibited by 29.36% and 29.72%, respectively. This suggests that the *Persicaria posumbu* 80% ethanol extract secretes CCK by acting as a G protein agonist and/or a PLCβ2 agonist.

Accordingly, it is expected that the *Persicaria posumbu* extract of the present disclosure can exhibit an effect of treating diabetes through increase of insulin gene expression, suppression of glucagon secretion, decrease of blood sugar level, etc. Also, it is expected that it can exhibit an effect of preventing obesity by suppressing appetite and increasing satiety.

In addition, it is expected that the *Persicaria posumbu* extract can exhibit an effect of improving digestion and malabsorption by regulating intestinal contraction and motility.

Change in Intracellular Calcium Level 4-4-4. Effect of *Persicaria posumbu* 80% Ethanol Extract on Change in $Ca^{2+}$ Level in STC-1 Cells

TABLE 35

| Sample | Concentration | ΔRFU (mean ± S.E.M.) | t-test | p value |
|---|---|---|---|---|
| Control | 0.5% DMSO | 75.93 ± 4.26 | | |
| *Persicaria posumbu* 80% ethanol extract | 100 µg/mL | 87.95 ± 1.33 | * | |
| | 250 µg/mL | 99.09 ± 1.72 | ** | |
| | 500 µg/mL | 100.11 ± 4.16 | ** | |

±S.E.M. (n = 9)  $p < 0.01$, * $p < 0.001$ vs. control (0.5% DMSO).

As seen from Table 35, the *Persicaria posumbu* 80% ethanol extract affected the release of calcium ions in a concentration-dependent manner. Accordingly, it is expected that the *Persicaria posumbu* extract can exhibit an effect of treating diabetes, suppressing appetite, preventing obesity and regulating digestion and malabsorption by affecting the activation of GPCRs.

4-4-5. Effect of Inhibitor on Change in $Ca^{2+}$ Level in STC-1 Cells by *Persicaria posumbu* 80% Ethanol Extract (1)

The STC-1 cells were pretreated for 60 minutes with 100 µM ruthenium red (RR) or with 50 µM HC-030031. Then, the cells were treated with 1 mg/mL of the extract.

TABLE 36

| Sample | Concentration | Inhibitor | ΔRFU (mean ± S.E.M.) | t-test | p value | Inhibition (%) |
|---|---|---|---|---|---|---|
| Control | 0.5% DMSO | | 34.34 ± 1.63 | | | |
| *Persicaria posumbu* 80% ethanol extract | 1 mg/mL | Untreated | 227.63 ± 5.08 | | | |
| | | RR | 107.71 ± 2.71 | *** | <0.001 | 52.68 |
| | | HC-030031 | 204.44 ± 4.89 | * | 0.05 | 10.19 |

±S.E.M. (n = 9) *** $p < 0.001$ vs. untreated.

As seen from Table 36, when the cells were incubated with the TRP antagonist RR or the TRPA1 antagonist HC-030031 together with the *Persicaria posumbu* 80% ethanol extract, the $Ca^{2+}$ release by the *Persicaria posumbu* 80% ethanol extract was inhibited by 52.68% and 10.19%, respectively. This suggests that the *Persicaria posumbu* 80% ethanol extract induces inflow of calcium ions from outside the cell membrane by acting as a TRP agonist or a TRPA1 agonist and thereby activating the TRP channels.

4-4-6. Effect of Inhibitor on Change in $Ca^{2+}$ Level in STC-1 Cells by *Persicaria posumbu* 80% Ethanol Extract (2)

The STC-1 cells were pretreated for 60 minutes with 400 µM TPPO or with 20 µM U-73122.

Then, the cells were treated with 1 mg/mL of the extract.

TABLE 37

| Sample | Concentration | Inhibitor | ΔRFU (mean ± S.E.M.) | t-test | p value | Inhibition (%) |
|---|---|---|---|---|---|---|
| Control | 0.5% DMSO | | 71.14 ± 7.10 | | | |
| *Persicaria posumbu* 80% ethanol extract | 1 mg/mL | Untreated | 230.39 ± 36.90 | | | |
| | | TPPO | 183.55 ± 5.53 | * | 0.05 | 20.33 |
| | | U-73122 | 48.85 ± 6.87 | ** | 0.008 | 78.80 |

±S.E.M. (n = 9) *** p < 0.001 vs. untreated.

As seen from Table 37, when the cells were incubated with the G protein inhibitor TPPO or the PLCβ2 Inhibitor U-73122 together with the *Persicaria posumbu* 80% ethanol extract, the $Ca^{2+}$ release by the *Persicaria posumbu* 80% ethanol extract was inhibited by 20.33% and 78.80%, respectively. This suggests that the *Persicaria posumbu* 80% ethanol extract increases the $Ca^{2+}$ concentration in the cytoplasm by acting as a G protein agonist and/or a PLCβ2 agonist. Accordingly, it is expected that the *Persicaria posumbu* extract will affect the activation of GPCRs.

From the results of Tables 36 and 37, it is expected that the *Persicaria posumbu* extract can exhibit an effect of treating diabetes, suppressing appetite, preventing obesity and regulating digestion and malabsorption.

4-4-7. Effect of *Persicaria posumbu* 80% Ethanol Extract on Membrane Potential Change in STC-1 Cells

TABLE 38

| Sample | Concentration | ΔRFU (mean ± SEM) | t-test | p value |
|---|---|---|---|---|
| Control | 0.5% DMSO | 59.12 ± 2.09 | | |
| *Persicaria posumbu* 80% ethanol extract | 500 µg/mL | 123.21 ± 2.62 | *** | <0.001 |

±S.E.M. (n = 0) p < 0.01, * p < 0.001 vs. control (0.5% DMSO).

As seen from Table 38, the *Persicaria posumbu* 80% ethanol extract affected the membrane potential change. It is though that the activation of GPCRs led to the Increased movement of ions in the cells. Accordingly, it is expected that the *Persicaria posumbu* extract can increase GLP-1 secretion by activating GPCRs and can exhibit an effect of treating diabetes, suppressing appetite, preventing obesity, regulating digestion and malabsorption, etc.

<5> *Geum aleppicum* Extract

Effect on CCK Secretion 4-5-1. Effect of *Geum aleppicum* 80% Ethanol Extract on CCK Secretion in STC-1 Cells

TABLE 39

| Sample | Concentration | Fold of control (mean ± S.E.M.) | t-test | p value |
|---|---|---|---|---|
| Control | | 1.00 ± 0.01 | | |
| *Geum aleppicum* 80% ethanol extract | 100 µg/mL | 20.37 ± 3.94 | ** | 0.008 |
| | 250 µg/mL | 33.12 ± 3.40 | *** | <0.001 |
| | 500 µg/mL | 60.49 ± 2.21 | *** | <0.001 |
| AITC | 0.1 mM | 21.57 ± 0.59 | *** | <0.001 |
| | 1 mM | 21.99 ± 0.64 | *** | <0.001 |
| | 10 mM | 25.59 ± 0.59 | *** | <0.001 |

Fold of control = sample value/untreated control value.
±S.E.M. (n = 9)  p < 0.01, * p < 0.001 vs. control (1% DMSO).

As seen from Table 39, the *Geum aleppicum* 80% ethanol extract increased CCK secretion in STC-1 cells.

4-5-2. Effect of Inhibitor on CCK Secretion in STC-1 Cells by *Geum aleppicum* 80% Ethanol Extract (1)

The STC-1 cells were pretreated for 30 minutes with 100 µM ruthenium red (RR) or with 50 µM HC-030031. Then, the cells were incubated at 37° C. for 60 minutes after adding 500 µg/mL of the extract.

TABLE 40

| Sample | Concentration | Inhibitor | Fold of control (mean ± S.E.M.) | t-test | p value | Inhibition (%) |
|---|---|---|---|---|---|---|
| Control | 1% DMSO | | 1.00 ± 0.04 | | | |
| *Geum aleppicum* 80% ethanol extract | 500 µg/mL | Untreated | 34.22 ± 0.98 | | | |
| | | RR | 12.22 ± 0.41 | *** | <0.001 | 64.29 |
| | | HC-030031 | 29.44 ± 0.82 | * | 0.02 | 13.97 |
| AITC | 0.1 mM | Untreated | 22.56 ± 0.65 | | | |
| | | RR | 6.04 ± 0.73 | *** | <0.001 | 73.21 |
| | | HC-030031 | 10.70 ± 0.92 | *** | <0.001 | 52.58 |

±S.E.M. (n = 9)  p < 0.05, * p < 0.001 vs. control.

As seen from Table 40, when the cells were incubated with the TRP antagonist RR or the TRPA1 antagonist HC-030031 together with the *Geum aleppicum* 80% ethanol extract, the CCK secretion by the *Geum aleppicum* 80% ethanol extract was inhibited by 47.89% and 6%, respectively. This suggests that the *Geum aleppicum* 80% ethanol extract secretes CCK by acting as a TRP agonist or a TRPA1 agonist.

Accordingly, it is expected that the *Geum aleppicum* extract of the present disclosure can exhibit an effect of treating diabetes through increase of insulin gene expression, suppression of glucagon secretion, decrease of blood sugar level, etc. Also, it is expected that it can exhibit an effect of preventing obesity by suppressing appetite and increasing satiety.

In addition, it is expected that the *Geum aleppicum* extract can exhibit an effect of Improving digestion and malabsorption by regulating intestinal contraction and motility.

4-5-3. Effect of Inhibitor on CCK Secretion in STC-1 Cells by *Geum aleppicum* 80% Ethanol Extract (2)

The STC-1 cells were pretreated for 30 minutes with 400 µM TPPO or with 20 µM U-73122.

Then, the cells were incubated at 37° C. for 60 minutes after adding 500 µg/mL of the extract.

TABLE 41

| Sample | Concentration | Inhibitor | Fold of control (mean ± S.E.M.) | t-test | p value | Inhibition (%) |
|---|---|---|---|---|---|---|
| Control | 1% DMSO | | 1.00 ± 0.07 | | | |
| *Geum aleppicum* 80% ethanol extract | 500 µg/mL | Untreated | 30.49 ± 0.45 | | | |
| | | TPPO | 21.19 ± 0.24 | *** | <0.001 | 30.50 |
| | | U-73122 | 14.35 ± 0.27 | *** | <0.001 | 52.93 |
| DB | 10 mM | Untreated | 25.01 ± 0.77 | | | |
| | | TPPO | 17.05 ± 0.03 | *** | <0.001 | 31.83 |
| | | U-73122 | 15.53 ± 0.01 | *** | <0.001 | 37.92 |

Fold of control = sample value/untreated control value
±S.E.M. (n = 9) *** $p < 0.001$ vs. untreated.

As seen from Table 41, when the cells were incubated with the G protein inhibitor TPPO or the PLCβ2 Inhibitor U-73122 together with the *Geum aleppicum* 80% ethanol extract, the CCK secretion by the *Geum aleppicum* 80% ethanol extract was inhibited by 30.50% and 52.93%, respectively. This suggests that the *Geum aleppicum* 80% ethanol extract secretes CCK by acting as a G protein agonist and/or a PLCβ2 agonist.

Accordingly, it is expected that the *Geum aleppicum* extract of the present disclosure can exhibit an effect of treating diabetes through increase of Insulin gene expression, suppression of glucagon secretion, decrease of blood sugar level, etc. Also, it is expected that it can exhibit an effect of preventing obesity by suppressing appetite and increasing satiety.

In addition, it is expected that the *Geum aleppicum* extract can exhibit an effect of improving digestion and malabsorption by regulating intestinal contraction and motility.

Change in Intracellular Calcium Level 4-5-4. Effect of *Geum aleppicum* 80% Ethanol Extract on Change in $Ca^{2+}$ Level in STC-1 Cells

TABLE 42

| Sample | Concentration | ΔRFU (mean ± S.E.M.) | t-test | p value |
|---|---|---|---|---|
| Control | 0.5% DMSO | 75.93 ± 4.26 | | |
| *Geum aleppicum* 80% ethanol extract | 100 µg/mL | 148.82 ± 4.69 | ** | 0.006 |
| | 250 µg/mL | 170.79 ± 2.46 | *** | 0.001 |
| | 500 µg/mL | 206.37 ± 5.37 | *** | <0.001 |
| AITC | 0.1 mM | 105.41 ± 2.12 | ** | 0.003 |
| | 1 mM | 151.04 ± 5.65 | *** | <0.001 |
| | 10 mM | 168.68 ± 5.79 | *** | <0.001 |

±S.E.M. (n = 9)  $p < 0.01$, * $p < 0.001$ vs. control (0.5% DMSO).

As seen from Table 42, the *Geum aleppicum* 80% ethanol extract affected the release of calcium ions in a concentration-dependent manner. Accordingly, it is expected that the *Geum aleppicum* extract can exhibit an effect of treating diabetes, suppressing appetite, preventing obesity and regulating digestion and malabsorption by affecting the activation of GPCRs.

4-5-5. Effect of Inhibitor on Change in $Ca^{2+}$ Level in STC-1 Cells by *Geum aleppicum* 80% ethanol extract (1)

The STC-1 cells were pretreated for 60 minutes with 100 µM ruthenium red or with 50 µM HC-030031. Then, the cells were treated with 1 mg/mL of the extract.

TABLE 43

| Sample | Conc. | Inhibitor | ΔRFU (mean ± S.E.M.) | t-test | p value | Inhibition (%) |
|---|---|---|---|---|---|---|
| Control | 0.5% DMSO | | 34.34 ± 1.63 | | | |
| *Geum aleppicum* 80% ethanol extract | 1 mg/mL | Untreated | 137.18 ± 3.10 | | | |
| | | RR | 17.25 ± 2.77 | *** | <0.001 | 87.43 |
| | | HC-030031 | 39.31 ± 1.02 | *** | | |
| AITC | 0.1 mM | Untreated | 400.52 ± 6.90 | | | |
| | | RR | 27.47 ± 1.77 | *** | <0.001 | 93.14 |
| | | HC-030031 | 66.07 ± 2.56 | *** | <0.001 | 83.50 |

±S.E.M. (n = 9) *** $p < 0.001$ vs. untreated.

As seen from Table 43, when the cells were incubated with the TRP antagonist RR or the TRPA1 antagonist HC-030031 together with the *Geum aleppicum* 80% ethanol extract, the $Ca^{2+}$ release by the *Geum aleppicum* 80% ethanol extract was inhibited by 52.68% and 10.19%, respectively. This suggests that the *Geum aleppicum* 80% ethanol extract induces inflow of calcium ions from outside the cell membrane by acting as a TRP agonist or a TRPA1 agonist and thereby activating the TRP channels.

4-5-6. Effect of Inhibitor on Chance in $Ca^{2+}$ Level in STC-1 Cells by *Geum aleppicum* 80% Ethanol Extract (2)

The STC-1 cells were pretreated for 60 minutes with 400 μM TPPO or with 20 μM U-73122. Then, the cells were treated with 1 mg/mL of the extract.

TABLE 44

| Sample | Concentration | Inhibitor | ΔRFU (mean ± S.E.M.) | t-test | p value | Inhibition (%) |
|---|---|---|---|---|---|---|
| Control | 0.5% DMSO | | 71.14 ± 7.10 | | | |
| Geum aleppicum 80% ethanol extract | 1 mg/mL | Untreated | 219.36 ± 31.64 | | | |
| | | TPPO | 126.38 ± 16.25 | ** | 0.853 | |
| | | U-73122 | 22.23 ± 2.35 | ** | 0.003 | 89.37 |
| DB | 10 mM | Untreated | 217.79 ± 15.99 | | | |
| | | TPPO | 100.56 ± 2.16 | ** | 0.002 | 53.83 |
| | | U-73122 | 130.60 ± 6.04 | ** | 0.007 | 40.03 |

±S.E.M. (n = 9) *** p < 0.001 vs. untreated.

As seen from Table 44, when the cells were incubated with the G protein inhibitor TPPO or the PLCβ2 Inhibitor U-73122 together with the *Geum aleppicum* 80% ethanol extract, the $Ca^{2+}$ release by the *Geum aleppicum* 80% ethanol extract was inhibited by 20.33% and 78.80%, respectively. This suggests that the *Geum aleppicum* 80% ethanol extract increases the $Ca^{2+}$ concentration in the cytoplasm by acting as a G protein agonist and/or a PLCβ2 agonist. Accordingly, it is expected that the *Geum aleppicum* extract affects the activation of GPCRs.

From the results of Tables 43 and 44, it is expected that the *Geum aleppicum* extract can exhibit an effect of treating diabetes, suppressing appetite, preventing obesity and regulating digestion and malabsorption.

4-5-7. Effect of *Geum aleppicum* 80% Ethanol Extract on Membrane Potential Change in STC-1 Cells

TABLE 45

| Sample | Concentration | ΔRFU (mean ± SEM) | t-test | p value |
|---|---|---|---|---|
| Control | 0.5% DMSO | 59.12 ± 2.09 | | |
| Geum aleppicum 80% ethanol extract | 500 μg/mL | 248.80 ± 3.25 | *** | <0.001 |
| KCl | 0.1 mM | 17.01 ± 0.93 | *** | <0.001 |
| | 1 mM | 35.08 ± 3.43 | ** | 0.004 |
| | 10 mM | 270.08 ± 9.57 | *** | <0.001 |

±S.E.M. (n = 3-4)  p < 0.01, * p < 0.001 vs. control (0.5% DMSO).

As seen from Table 45, the *Geum aleppicum* 80% ethanol extract affected the membrane potential change. It is though that the activation of GPCRs led to the increased movement of ions in the cells. Accordingly, it is expected that the *Geum aleppicum* extract can increase GLP-1 secretion by activating GPCRs and can exhibit an effect of treating diabetes, suppressing appetite, preventing obesity, regulating digestion and malabsorption, etc.

Example 5. Measurement of 5-HT Using RIN14B Cells

1. Cell Culturing

RIN14B cells were cultured in RPMI medium 1640 containing 10% fetal bovine serum (FBS) and 1% penicillin-streptomycin in an incubator maintained at 37° C. and 5% $CO_2$.

The fetal bovine serum (FBS), the penicillin-streptomycin and the Dulbecco's modified Eagle's medium (DMEM) used for the culturing were purchased from Gibco.

2. Measurement of 5-HT Secretion

The cultured cells were inoculated onto a 24-well plate at a concentration of $2 \times 10^5$ cells/well and incubated under the condition of 37° C. and 5% $CO_2$. 72 hours later, the cells were washed 2 times with 5-HT assay buffer (HBSS, 0.1% BSA, 1.25 mM $CaCl_2$, 2 μM fluoxetine, pH 7.4) and then incubated at 37° C. for 60 minutes after adding the test substance to the 5-HT assay buffer. After the incubation, the medium was centrifuged at 10,000 rpm for 10 minutes and the resultant supernatant was stored at −70° C. for use in analysis. A Serotonin (EIA) kit (Enzo Life Sciences) was used.

3. Measurement of Change in Intracellular Calcium Level

The cells were inoculated onto a black 96-well clear-bottom plate (Corning) at a concentration of $5.0 \times 10^4$ cells/well and incubated under the condition of 37° C. and 5% $CO_2$. 48 hours later, the cells were incubated at 37° C. for 60 minutes using the Calcium-5 assay kit (Molecular Devices) and the change in $Ca^{2+}$ level was measured using Flexstation III. The change in $Ca^{2+}$ level was monitored for about 120 seconds at fluorescence wavelengths of 488 nm (ex) and 525 nm (em) and for 2 seconds after injecting the compound for 20 seconds.

4. Result

<1> *Oldenlandia brachypoda* Extract 5-1-1. Effect of *Oldenlandia brachypoda* 80% Ethanol Extract on 5-HT Secretion in RIN14B Cells

TABLE 46

| Sample | Concentration | Fold of control (mean ± S.E.M.) | t-test | p value |
|---|---|---|---|---|
| Control | 1% DMSO | 1.00 ± 0.26 | | |
| Oldenlandia brachypoda 80% ethanol extract | 100 μg/mL | 5.89 ± 0.46 | *** | <0.001 |
| | 250 μg/mL | 19.85 ± 2.32 | ** | 0.001 |
| | 500 μg/mL | 36.19 ± 2.06 | *** | <0.001 |
| AITC | 300 μM | 8.11 ± 2.70 | | |

Fold of control = sample value/untreated control value.
Values are presented as the mean ± S.E.M. (n = 9)  p < 0.01, * p < 0.001 vs. control.

As seen from Table 46, the *Oldenlandia brachypoda* extract affected 5-HT secretion which is known to effectively regulate digestion and absorption.

5-1-2. Effect of *Oldenlandia brachypoda* 80% Ethanol Extract on Change in $Ca^{2+}$ Level in RIN14B Cells

TABLE 47

| Sample | Concentration | ΔRFU (mean ± S.E.M.) | t-test | p value |
|---|---|---|---|---|
| Control | 0.5% DMSO | 3.34 ± 0.44 | | |
| *Oldenlandia brachypoda* 80% ethanol extract | 100 μg/mL | 10.04 ± 0.65 | *** | <0.001 |
| | 250 μg/mL | 16.32 ± 1.00 | *** | <0.001 |
| | 500 μg/mL | 28.10 ± 0.78 | *** | <0.001 |
| AITC | 50 μM | 13.44 ± 1.78 | ** | 0.005 |
| | 300 μM | 19.78 ± 4.08 | * | 0.017 |
| | 500 μM | 22.17 ± 3.65 | *** | 0.007 |

ΔRFU was determined for each well.
±S.E.M. (n = 9) * p < 0.05,  p < 0.01, * p < 0.001 vs. control.

As seen from Table 47, the RIN14B cells treated with the *Oldenlandia brachypoda* extract showed a larger ΔRFU value than those treated with AITC which is known to promote 5-HT secretion. Accordingly, it is expected that the *Oldenlandia brachypoda* extract can exhibit an anti-obesity effect by affecting the activation of TRP channels involved in CCK secretion and thereby suppressing appetite. It is also expected that it will allow for effective regulation of digestion and absorption.

<2> *Spergularia Marina* Extract
Measurement of Effect on 5-HT Secretion
5-2-1. Effect of *Spergularia marina* 50% Ethanol Extract on 5-HT Secretion in RIN14B Cells

TABLE 48

| Sample | Concentration | Fold of control (mean ± SEM) | t-test | p value |
|---|---|---|---|---|
| Control | 1% DMSO | 1.00 ± 0.26 | | |
| *Spergularia marina* 50% ethanol extract | 500 μg/mL | 2.51 ± 0.35 | * | 0.05 |

Fold of control = sample value/untreated control value.
Values are presented as the mean ± S.E.M. (n = 9).

As seen from Table 48, the *Spergularia marina* extract affected 5-HT secretion which is known to effectively regulate digestion and absorption, suppress appetite, etc.

5-2-2. Effect of 5 Fractions of *Spergularia marina* 50% Ethanol Extract on 5-HT Secretion

TABLE 49

| sample | Fraction | Concentration (μg/mL) | Fold of control (mean ± S.E.M.) | t-test | p value |
|---|---|---|---|---|---|
| Control | | 1% DMSO | 1.00 ± 0.19 | | |
| *Spergularia marina* 50% ethanol extract | Before fractionation | 100 | 2.51 ± 0.04 | | |
| | Hexane layer | 100 | 59.50 ± 1.07 | *** | <0.001 |
| | Chloroform layer | 100 | 41.68 ± 3.96 | *** | <0.001 |
| | Ethyl acetate layer | 100 | 2.91 ± 0.02 | *** | <0.001 |
| | Butanol layer | 100 | 2.65 ± 0.22 | | 0.549 |
| | Distilled water layer | 100 | 2.13 ± 0.23 | | 0.172 |

Fold of control = sample value/untreated control value.
±S.E.M. (n = 9) *** p < 0.001 vs. before fractionation.

As seen from Table 49, the hexane fraction and the chloroform fraction of the *Spergularia marina* extract exhibited better effect of increasing 5-HT secretion than the *Spergularia marina* extract. Accordingly, it is expected that the hexane fraction and the chloroform fraction of the *Spergularia marina* extract will exhibit an effect of regulating digestion and absorption, suppressing appetite, preventing obesity, etc. by increasing 5-HT secretion.

5-2-3. Effect of *Spergularia marina* 50% Ethanol Extract on Chance in $Ca^{2+}$ Level in RIN14B Cells

TABLE 50

| Sample | Concentration | ΔRFU (mean ± S.E.M.) | t-test | p value |
|---|---|---|---|---|
| Control | 0.5% DMSO | 3.34 ± 0.44 | | |
| *Spergularia marina* 50% ethanol extract | 500 μg/mL | 32.45 ± 1.90 | *** | <0.001 |
| AITC | 50 μM | 13.44 ± 1.78 | ** | 0.005 |
| | 300 μM | 19.78 ± 4.08 | * | 0.017 |
| | 500 μM | 22.17 ± 3.65 | *** | 0.007 |

ΔRFU was determined for each well.
±S.E.M. (n = 3-4) * p < 0.05,  p < 0.01, * p < 0.001 vs. control.

As seen from Table 50, the RIN14B cells treated with the *Spergularia marina* extract showed a larger ΔRFU value than those treated with AITC which is known to promote 5-HT secretion. Accordingly, it is expected that the *Spergularia marina* extract can exhibit an anti-obesity effect by affecting the activation of TRP channels involved in CCK secretion.

5-2-4. Effect of 5 Fractions of *Spergularia marina* 50% Ethanol Extract on Change in $Ca^{2+}$ Level RIN14B Cells (Control Group: 0.5% DMSO, Sample Concentration: 500 μg/mL)

TABLE 51

| Sample | Fraction | ΔRFU (mean ± S.E.M.) | t-test | p value |
|---|---|---|---|---|
| Control | 0.5% DMSO | 4.19 ± 0.82 | | |
| *Spergularia marina* 50% ethanol extract | Before fractionation | 24.53 ± 1.32 | | |
| | Hexane layer | 54.02 ± 2.06 | *** | <0.001 |
| | Chloroform layer | 70.24 ± 1.38 | *** | <0.001 |
| | Ethyl acetate layer | 39.96 ± 0.64 | *** | <0.001 |
| | Butanol layer | 42.13 ± 2.34 | *** | <0.001 |
| | Distilled water layer | 34.39 ± 2.00 | ** | 0.006 |

ΔRFU was determined for each well.
±S.E.M. (n = 3-4)  p < 0.01, * p < 0.001 vs. before fractionation.

As seen from Table 51, the fractions of the *Spergularia marina* extract had a larger effect on the change in calcium level as compared to the extract before fractionation. This result suggests that the fractions of the *Spergularia marina* extract have better effect of inducing the change in $Ca^{2+}$ ion level. Since the change in $Ca^{2+}$ ion level means the activation of GPCRs, it is expected that the *Spergularia marina* extract can prevent obesity by activating GPCRs and thereby promoting GLP-1 secretion.

<3> *Disporum smilacinum* Extract 5-3-1. Effect of *Disporum smilacinum* 50% Ethanol Extract on 5-HT Secretion in RIN14B Cells

TABLE 52

| Sample | Concentration | Fold of control (mean ± SEM) | t-test | p value |
|---|---|---|---|---|
| Control | 1% DMSO | 1.00 ± 0.26 | | |
| *Disporum smilacinum* 50% ethanol extract | 500 µg/mL | 8.25 ± 0.17 | ** | 0.01 |
| AITC | 300 µM | 8.11 ± 2.70 | ** | 0.01 |

Fold of control = sample value/untreated control value.
Values are presented as the mean ± S.E.M. (n = 9)  p < 0.01, *p < 0.001 vs. control.

As seen from Table 52, the *Disporum smilacinum* extract affected 5-HT secretion which is known to exhibit an anti-obesity effect by suppressing appetite.

5-3-2. Effect of *Disporum smilacinum* 50% Ethanol Extract on Change in $Ca^{2+}$ Level in RIN14B Cells

TABLE 53

| Sample | Concentration | ΔRFU (mean ± S.E.M.) | t-test | p value |
|---|---|---|---|---|
| Control | 0.5% DMSO | 3.34 ± 0.44 | | |
| *Disporum smilacinum* 50% ethanol extract | 500 µg/mL | 18.02 ± 0.72 | *** | <0.001 |
| AITC | 50 µM | 13.44 ± 1.78 | ** | 0.005 |

ΔRFU was determined for each well.
±S.E.M. (n = 9) *p < 0.05,  p < 0.01, * p < 0.001 vs. control.

As seen from Table 53, the RIN14B cells treated with the *Disporum smilacinum* extract showed a larger ΔRFU value than those treated with AITC which is known to promote 5-HT secretion. This result suggests that the *Disporum smilacinum* extract affects the activation of TRP channels involved in CCK secretion.

<4> *Persicaria posumbu* Extract 5-4-1. Effect of *Persicaria posumbu* 804, Ethanol Extract on 5-HT Secretion in RIN14B Cells

TABLE 54

| Sample | Concentration | Fold of control (mean ± S.E.M.) | t-test | p value |
|---|---|---|---|---|
| Control | 1% DMSO | 1.00 ± 0.26 | | |
| *Persicaria posumbu* 80% ethanol extract | 500 µg/mL | 2.90 ± 0.09 | *** | <0.001 |

Fold of control = sample value/untreated control value
Values are presented as the mean ± S.E.M. (n = 9) *** p < 0.001 vs. control.

As seen from Table 54, the *Persicaria posumbu* extract affected 5-HT secretion which is known to effectively regulate digestion and absorption and prevent obesity by suppressing appetite.

5-4-2. Effect of *Persicaria posumbu* 80% Ethanol Extract on Change in $Ca^{2+}$ Level in RIN14B Cells

TABLE 55

| Sample | Concentration | ΔRFU (mean ± S.E.M.) | t-test | p value |
|---|---|---|---|---|
| Control | | 3.34 ± 0.44 | | |
| *Persicaria posumbu* 80% ethanol extract | 500 µg/mL | 67.81 ± 1.29 | *** | <0.001 |

ΔRFU was determined for each well.
±S.E.M. (n = 9) *p < 0.05, p < 0.01, * p < 0.001 vs. control.

As seen from Table 55, the RIN14B cells treated with the *Persicaria posumbu* extract showed a larger ΔRFU value than those treated with AITC which is known to promote 5-HT secretion. This result suggests that the *Persicaria posumbu* extract affects the activation of TRP channels involved in CCK secretion. Accordingly, it is expected that the *Persicaria posumbu* extract can exhibit an anti-obesity effect by suppressing appetite and allow for effective regulation of digestion and absorption.

<5> *Geum aleppicum* Extract 5-5-1. Effect of *Geum aleppicum* 80% Ethanol Extract on 5-HT Secretion in RIN14B Cells

TABLE 56

| Sample | Concentration | Fold of control (mean ± S.E.M.) | t-test | p value |
|---|---|---|---|---|
| Control | 1% DMSO | 1.00 ± 0.26 | | |
| *Geum aleppicum* 80% ethanol extract | 100 µg/mL | 10.54 ± 0.36 | *** | <0.001 |
| | 250 µg/mL | 24.46 ± 2.14 | *** | <0.001 |
| | 500 µg/mL | 33.29 ± 0.38 | *** | <0.001 |
| AITC | 300 µM | 8.11 ± 2.70 | | |

Fold of control = sample value/untreated control value.
Values are presented as the mean ± S.E.M. (n = 9) *** p < 0.001 vs. control.

As seen from Table 56, the *Geum aleppicum* extract affected 5-HT secretion which is known to effectively regulate digestion and absorption and prevent obesity by suppressing appetite.

5-5-2. Effect of Inhibitor on 5-HT Secretion by *Geum aleppicum* 80% Ethanol Extract in RIN14B Cells The RIN14B cells were pretreated for 30 minutes with 100 µM ruthenium red (RR) or with 50 µM HC-030031. After adding 500 µg/mL of the extract, the cells were incubated at 37° C. for 60 minutes.

TABLE 57

| Sample | Concentration | Inhibitor | Fold of control (mean ± S.E.M.) | t-test | p value | Inhibition (%) |
|---|---|---|---|---|---|---|
| Control | 1% DMSO | | 1.00 ± 0.19 | | | |
| *Geum aleppicum* 80% ethanol extract | 500 µg/mL | Untreated | 35.34 ± 4.03 | | | |
| | | RR | 12.20 ± 6.45 | | | 65.49 |
| | | HC-030031 | 17.38 ± 9.21 | | | 50.82 |

TABLE 57-continued

| Sample | Concentration | Inhibitor | Fold of control (mean ± S.E.M.) | t-test | p value | Inhibition (%) |
|---|---|---|---|---|---|---|
| AITC | 300 μM | Untreated | 8.11 ± 2.70 | | | |
| | | RR | 3.60 ± 1.80 | | | 55.56 |
| | | HC-030031 | 9.02 ± 6.37 | | | −11.27 |

Fold of control = sample value/untreated control value.
Values are presented as the mean ± S.E.M. (n = 3-4).

As seen from Table 57, when the cells were incubated with the TRP antagonist RR or the TRPA1 antagonist HC-030031 together with the *Geum aleppicum* 80% ethanol extract, the 5-HT secretion by the *Geum aleppicum* 80% ethanol extract was inhibited by 65.49% and 50.82%, respectively. This suggests that the *Geum aleppicum* 80% ethanol extract induces inflow of calcium ions from outside the cell membrane by acting as a TRP agonist or a TRPA1 agonist and thereby activating the TRP channels.

5-5-3. Effect of *Geum aleppicum* 80% Ethanol Extract on Change in $Ca^{2+}$ Level in RIN14B Cells

TABLE 58

| Sample | Concentration | ΔRFU (mean ± S.E.M.) | t-test | p value |
|---|---|---|---|---|
| Control | 0.5% DMSO | 3.34 ± 0.44 | | |
| *Geum aleppicum* 80% ethanol extract | 100 μg/mL | 11.08 ± 0.74 | *** | <0.001 |
| | 250 μg/mL | 25.24 ± 0.23 | *** | <0.001 |
| | 500 μg/mL | 37.04 ± 1.28 | *** | <0.001 |

ΔRFU was determined for each well.
±S.E.M. (n = 9) *p < 0.05, p < 0.01, * p < 0.001 vs. control.

As seen from Table 58, the RIN14B cells treated with the *Geum aleppicum* extract showed a larger ΔRFU value as compared to the untreated control group. This result suggests that the *Geum aleppicum* extract affects the activation of TRP channels involved in CCK secretion.

5-5-4. Effect of Inhibitor on Chance in $Ca^{2+}$ Level by *Geum aleppicum* 80% Ethanol Extract in RIN14B Cells The RIN14B cells were pretreated for 60 minutes with 100 μM ruthenium red (RR) or with 50 μM HC-030031. Then, 500 μg/mL of the extract was added.

TABLE 59

| Sample | Concentration | Inhibitor | ΔRFU (mean ± S.E.M.) | t-test | p value | Inhibition (%) |
|---|---|---|---|---|---|---|
| Control | 0.5% DMSO | | 3.61 ± 0.15 | | | |
| *Geum aleppicum* 80% ethanol extract | 500 μg/mL | Untreated | 24.99 ± 0.88 | | | |
| | | RR | 12.68 ± 2.41 | ** | 0.003 | 49.24 |
| | | HC-030031 | 11.11 ± 0.92 | ** | 0.003 | |
| AITC | 300 μM | Untreated | 13.42 ± 1.08 | | | |
| | | RR | 4.51 ± 1.40 | ** | 0.005 | 66.36 |
| | | HC-030031 | 3.98 ± 0.80 | *** | <0.001 | 70.31 |

±S.E.M. (n = 9)  p < 0.01, * p < 0.001 vs. untreated.

As seen from Table 59, when the cells were incubated with the TRP antagonist RR or the TRPA1 antagonist HC-030031 together with the *Geum aleppicum* 80% ethanol extract, the $Ca^{2+}$ release by the *Geum aleppicum* 80% ethanol extract was inhibited by 52.68% and 10.19%, respectively. This suggests that the *Geum aleppicum* 80% ethanol extract induces inflow of calcium ions from outside the cell membrane by acting as a TRP agonist or a TRPA1 agonist and thereby activating the TRP channels.

Example 6. Animal Experiment Using Extracts of the Present Disclosure

The *Oldenlandia brachypoda* extract, the *Spergularia marina* extract, the *Disporum smilacinum* extract, the *Persicaria posumbu* extract and the *Geum aleppicum* extract obtained in Example 1 were dissolved in distilled water and orally administered to experimental rats for 1) monitoring of neuronal activation by immunostaining of brain tissue, 2) glucose tolerance test, 3) measurement of gastric emptying rate, 4) measurement of food intake and 5) measurement of chloride excretion.

(1) Experimental Methods
1) Monitoring of Neuronal Activation by Immunostaining of Brain Tissue After intragastrically administering each of the *Oldenlandia brachypoda* extract, the *Spergularia marina* extract, the *Disporum smilacinum* extract, the *Persicaria posumbu* extract and the *Geum aleppicum* extract, c-Fos immunostaining was conducted for analysis of the activation of brain parts. The experimental animals were fasted for 12 hours and orally administrated with each of the extract dissolved in distilled water (500 mg/kg BW). 2 hours later, the rats were deeply anesthetized with urethane. After transcardially perfusing 200 mL cold PBS followed by 300 mL of 4% paraformaldehyde, brains were removed, immersed in 4% paraformaldehyde for 4 hours at 4° C., and then transferred to a 30% sucrose solution. The fixed brain tissues were frozen using an OCT solution. The frozen tissues were sectioned around the target areas at −20° C. with a thickness of 30 μm. The target areas were the arcuate nucleus (ARC) in the hypothalamus and the dorsal vagal complex (DVC). The sectioned tissues were washed with PBS. The tissues were immersed in 0.3% $H_2O_2$ for 15 minutes and then washed 3 times with PBS. The tissues were incubated for 30 minutes in PBS containing 3% normal goat serum. The tissues were diluted 1.1000 with polyclonal rabbit c-Fos antibodies (sc-25, Santa Cruz Biotech, USA) using PBST containing 3% normal goat serum without purification and then incubated at room temperature for 24 hours. After the incubation, the tissues were washed 3 times with PBST for 10 minutes. Then, the tissues were incubated again with anti-rabbit antibodies (BA-1000, Vector, USA) for 30 minutes at room temperature and then washed 3 times for 5 minutes. The tissues were incubated with avidin-biotinylated horseradish peroxidase complex (ABC) (PK-6100, Vector, USA) at room temperature for 30 minutes. After washing 3 times with PBST for 5 minutes and staining using a DAB kit (Zytomed Systems, Germany), the reaction was terminated with PBS. The stained tissues were transferred onto slides and then dehydrated after sufficient drying. The dehydrated slides were observed under a microscope after covering with cover slides.

The target areas of the stained tissues were determined according to the coordinates of Paxinos and Watson using a microscope (AXio. 4. 8. 1, Zeiss, Germany) and the number of the nuclei stained with the c-Fos antibody was counted and averaged for 3-6 slides.

2) Oral Glucose Tolerance Test in Rats

Sprague-Dawley rats (body weight ~400 g; male) were fasted for 16 hours and then orally administered with glucose (2 g/kg body weight) and with each of the *Oldenlandia brachypoda* extract, the *Spergularia marina* extract, the *Disporum smilacinum* extract, the *Persicaria posumbu* extract and the *Geum aleppicum* extract (500 mg/kg BW). 0, 30, 60, 90 and 120 minutes after the administration, blood was taken from the tail end and blood sugar level was measured using the Accu-Chek blood sugar meter (Roche). Rats administered only with glucose (2 g/kg body weight) were used as a control group.

3) Effect of Slowing Gastric Emptying Rate

Gastric emptying rate was measured using the methods of Izbeki and Doihara (1, 2). The rats were fasted for a day and then orally administered with each of the *Oldenlandia brachypoda* extract, the *Spergularia marina* extract, the *Disporum smilacinum* extract, the *Persicaria posumbu* extract and the *Geum aleppicum* extract (100, 250, 500 mg/kg BW) dissolved in distilled water. 30 minutes later, a 0.05% phenol red solution (1.5 mL) was orally administered to the rats. 20 minutes later, after cervical dislocation, the stomach was removed, washed with physiological saline and then immediately homogenized finely in a 0.1 N NaOH (100 mL). After stabilizing for 1 hour at room temperature, the supernatant (5 mL) was mixed with 20% trichloroacetic acid (0.5 mL) and then centrifuged for 20 minutes at 4° C. with 3000 rpm. The resulting supernatant was mixed with 0.5 N NaOH (4 mL) and absorbance was measured at 560 nm using a UV spectrophotometer. The same procedure was applied to the control group to which distilled water was orally administered.

REFERENCES (1) F. Izbeki, T. Wittmann, S. Csati, J. Lonovics. 2004. The mechanism of the inhibitory effect of ethanol on gastric emptying involve type A CCK receptors. *Regulatory Peptides*. 117: 101-105.

(2) H. Doihara, K. Nosawa, E. Kawabata-Shoda, R. Kojima, T. Yokoyama, H. Ito. 2009. TRPA1 agonists delay gastric emptying in rats through serotonergic pathways. *Naunyn-Schmied Arch Pharmacol*. 380: 353-357.

Gastric emptying rate was calculated as follows.

Gastric emptying rate (%)=100($A/B$)×100.

A: the amount of phenol red remaining in the gastrointestinal tract of the test group 20 minutes after the oral administration of the phenol red solution B: the amount of phenol red in the gastrointestinal tract of the control group immediately after the oral administration of the phenol red solution 4) Measurement of Food Intake For measurement of food intake, the rats were fasted for a day after intragastrically administering each of the *Oldenlandia brachypoda* extract, the *Spergularia marina* extract, the *Disporum smilacinum* extract, the *Persicaria posumbu* extract and the *Geum aleppicum* extract. Food intake was measured 120 minutes after oral administration of each of the *Oldenlandia brachypoda* extract, the *Spergularia marina* extract, the *Disporum smilacinum* extract, the *Persicaria posumbu* extract and the *Geum aleppicum* extract (500 mg/kg) dissolved in distilled water to 5 rats per each group (3). The same procedure was applied to the control group to which distilled water was orally administered.

REFERENCE (3) A. Serrano, F J. Pav, S. Tovar, F. Casanueva, R. Se, C. Di, F. R. Fonseca. 2011. Oleoylethanolamide: Effects on hypothalamic transmitters and gut peptides regulating food intake. *Neuropharmacology* 60: 593-601.

5) Effect on Chloride Excretion

For measurement of chloride content in serum, the rats were fasted for a day. After oral administration of each of the *Oldenlandia brachypoda* extract, the *Spergularia marina* extract, the *Disporum smilacinum* extract, the *Persicaria posumbu* extract and the *Geum aleppicum* extract (500 mg/kg BW) to 5 rats per each group, blood was taken from the eye socket 30 minutes later. The blood was kept at room temperature for 30 minutes. After centrifuging at 3,000 rpm for 15 minutes, the separated serum was subjected to measurement using a chloride assay kit (BioAssay Systems, USA).

(2) Experimental Results

1) Result of Monitoring Neuronal Activation by Immunostaining of Brain Tissue

After intragastrically administering each of the *Oldenlandia brachypoda* extract, the *Spergularia marina* extract, the *Disporum smilacinum* extract, the *Persicaria posumbu* extract and the *Geum aleppicum* extract, the activation of brain parts was analyzed by c-Fos immunostaining. When GLP-1, CCK, 5-HT, etc. are secreted into bloodstream in the intestine due to stimulation by the extract, they act as both hormones and neuropeptides. The GLP-1, CCK, 5-HT, etc. directly activate the arcuate nucleus (ARC) in the hypothalamus in the brain by acting as hormones. The GLP-1, CCK, 5-HT, etc. activate the vagus nerve, which activates the dorsal vagal complex (DVC), which again activates the arcuate nucleus (ARC) in the hypothalamus. In this way, the information about food intake is transmitted to the brain and the brain regulates physical activities by transmitting commands related homeostasis to peripheral tissues (Yi C-X and Tschop M H, Brain-gut-adipose-tissue communication pathways at a glance. *Disease Models & Mechanisms*, 5, 583, 2012).

Figure 2:
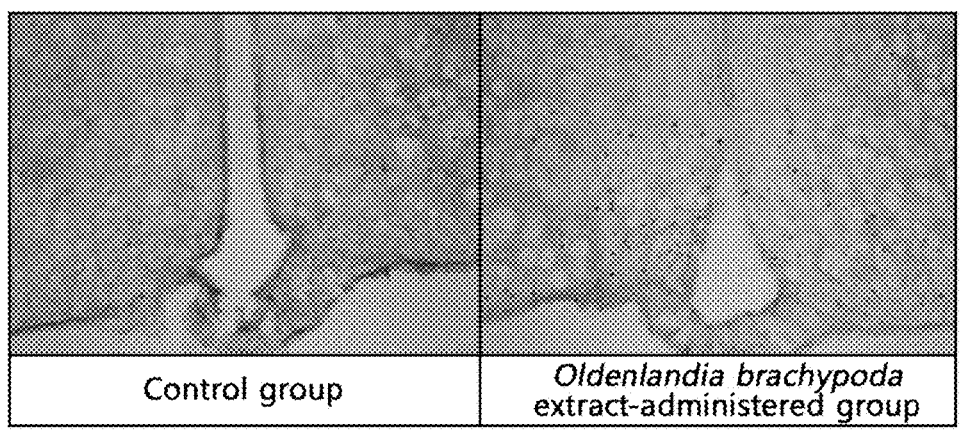
FIG. 2 shows activation of c-Fos in the arcuate nucleus (ARC) in the hypothalamus after administration of an *Oldenlandia brachypoda* extract.
Figure 3:
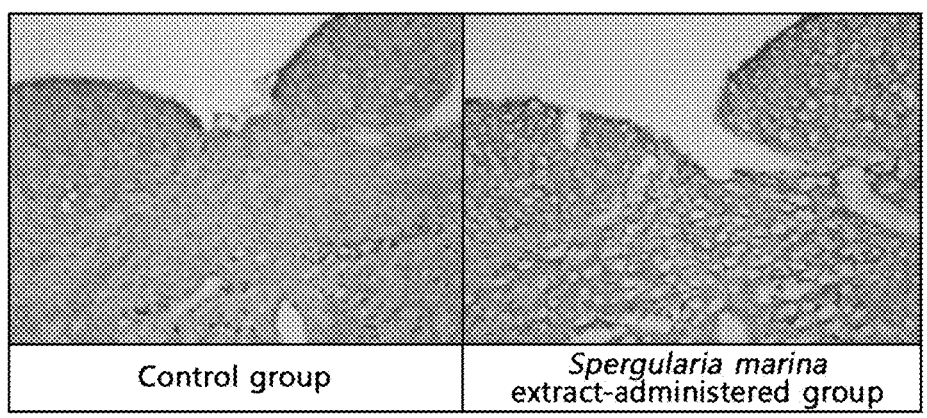
FIG. 3 shows activation of c-Fos in the caudal DVC (dorsal vagal complex) after administration of a *Spergularia marina* extract.
Figure 4:
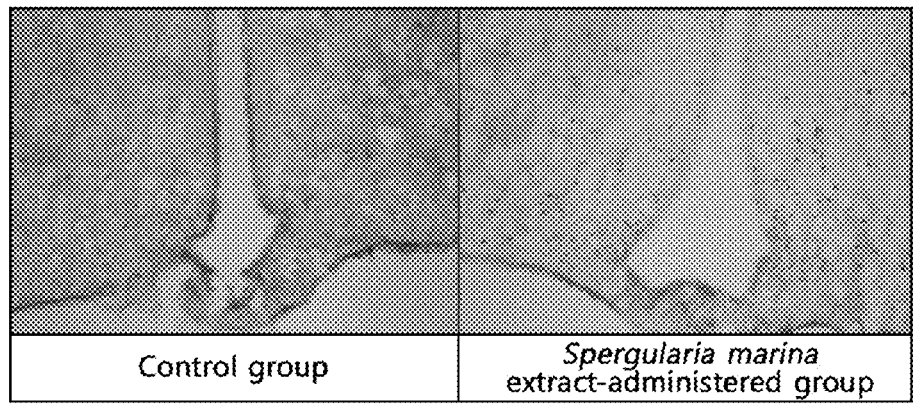
FIG. 4 shows activation of c-Fos in the arcuate nucleus (ARC) in the hypothalamus after administration of a *Spergularia marina* extract.
Figure 5:
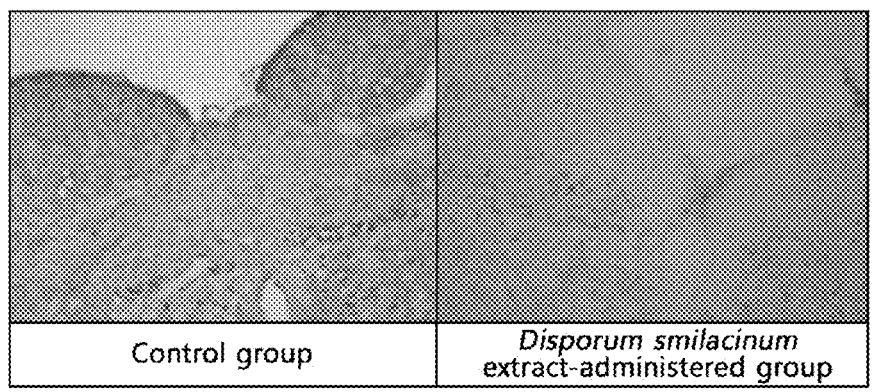
FIG. 5 shows activation of c-Fos in the caudal DVC (dorsal vagal complex) after administration of a *Disporum smilacinum* extract.
Figure 6:
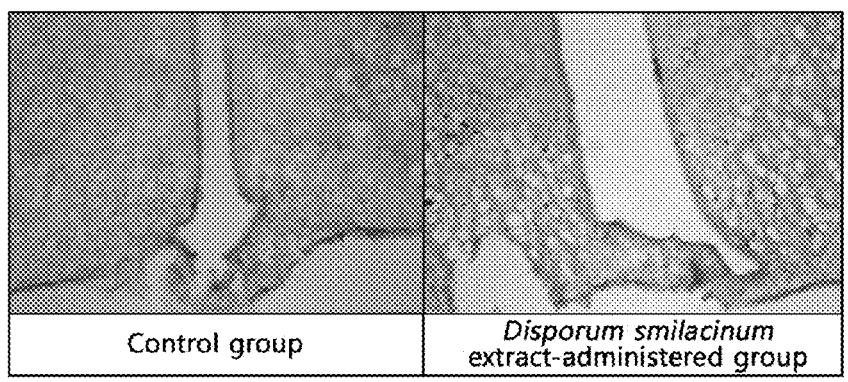
FIG. 6 shows activation of c-Fos in the arcuate nucleus (ARC) in the hypothalamus after administration of a *Disporum smilacinum* extract.
Figure 7:
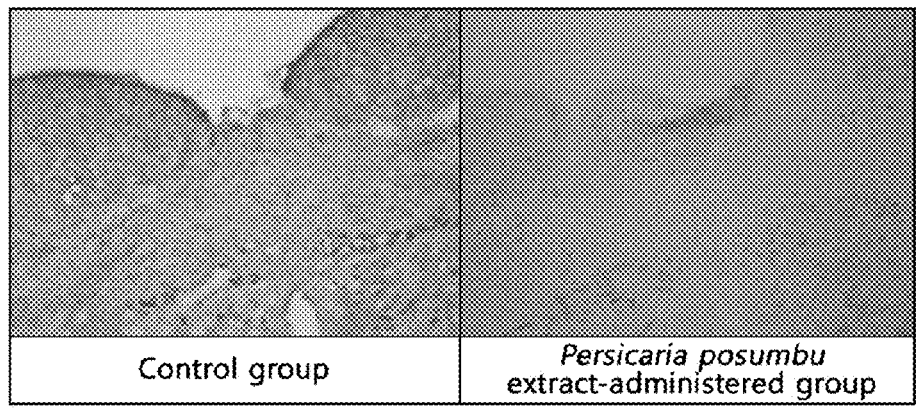
FIG. 7 shows activation of c-Fos in the caudal DVC (dorsal vagal complex) after administration of a *Persicaria posumbu* extract.
Figure 8:
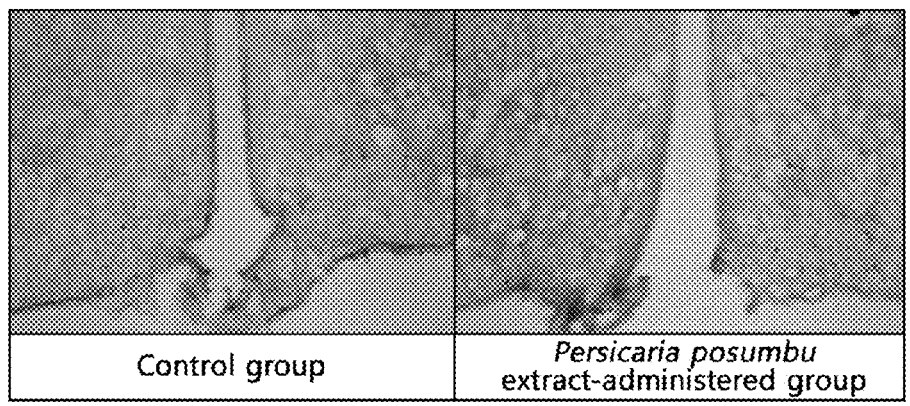
FIG. 8 shows activation of c-Fos in the arcuate nucleus (ARC) in the hypothalamus after administration of a *Persicaria posumbu* extract.
Figure 9:
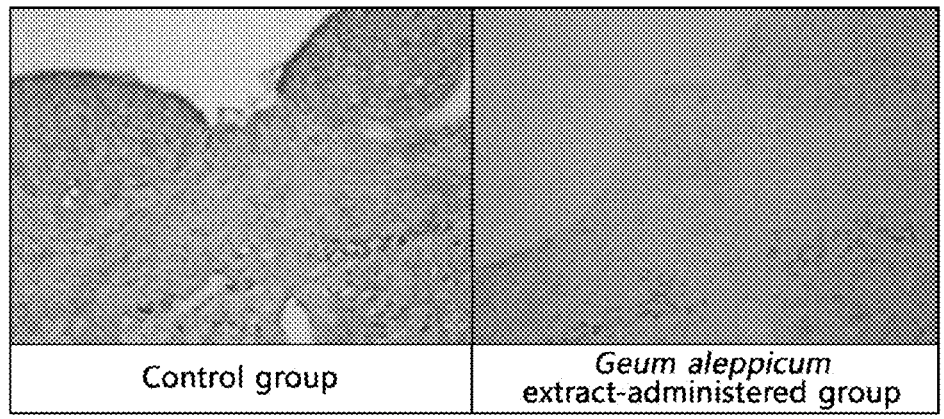
FIG. 9 shows activation of c-Fos in the caudal DVC (dorsal vagal complex) after administration of a *Geum aleppicum* extract.
Figure 10:
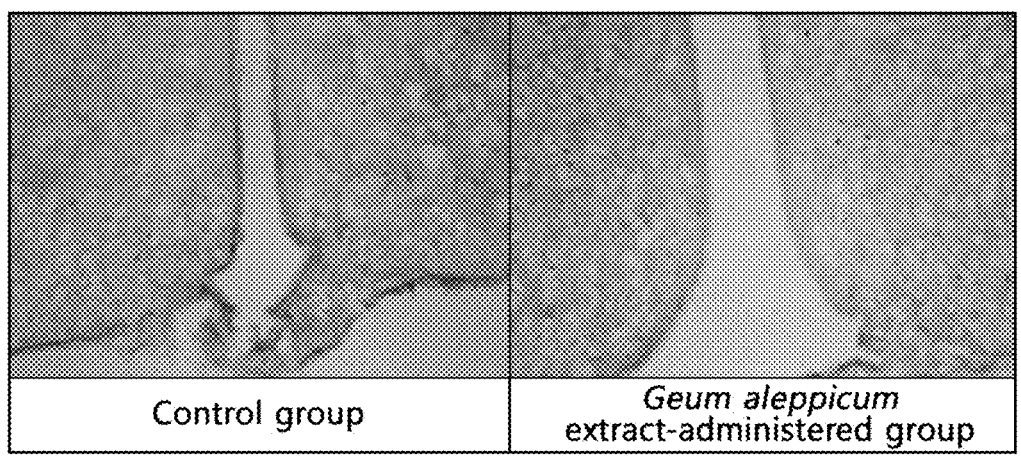
FIG. 10 shows activation of c-Fos in the arcuate nucleus (ARC) in the hypothalamus after administration of a *Geum aleppicum* extract.

As a result, the extracts activated c-Fos in the DVC and the ARC as indicated by black dots (see FIGS. 1-10). This means that various homeostasis-related activities occurred due to the secretion of GLP-1. CCK, 5-HT, etc.

2) Effect on Oral Glucose Tolerance Test in Rats (Anti-Diabetic Effect)

The effect of the extracts of the present disclosure on blood sugar increase was evaluated.

<1> *Oldenlandia brachypoda* Extract

The *Oldenlandia brachypoda* extract of the present disclosure showed 46.5% less increase in blood sugar level (54.9 mg/dL) as compared to the control group (102.7 mg/dL) after 30 minutes and 23.3% less increase in blood sugar level (84.9 mg/dL) as compared to the control group (110.7 mg/dL). The area under the curve (AUC) was 20% smaller as 13961 mg/dL min compared to the control group (17465 mg/dL min). The result is summarized in Table 60.

[Table 60]
Effect of *Oldenlandia brachypoda* Extract on Blood Sugar Increase in Rats Due to Oral Glucose Tolerance

| Test group[1] | Blood sugar level with time (mg/dL) | | | | | AUC[2] |
|---|---|---|---|---|---|---|
| | 0 minute | 30 minutes | 60 minutes | 90 minutes | 120 minutes | |
| Control[3] | 65.3 ± 5.9 | 168 ± 22.9 | 176 ± 14.7 | 130 ± 15.1 | 121 ± 11.2 | 17465 ± 1500 |
| *Oldenlandia brachypoda* extract | 70.1 ± 2.7 | 125 ± 12.5 | 155 ± 17.3 | 119 ± 9.1 | 120 ± 11.0 | 13961 ± 1112 |

[1]Values are mean ± SD (n = 10).
[2]AUC: Area under the curve (area under the blood sugar curve for 120 minutes due to glucose tolerance in min mg/dL unit).
[3]Glucose-administered group.

<2> *Spergularia marina* Extract

The *Spergularia marina* extract of the present disclosure showed 38.5% less increase in blood sugar level (63.2 mg/dL) as compared to the control group (102.7 mg/dL) after 30 minutes and 31.2% less increase in blood sugar level (76.2 mg/dL) as compared to the control group (110.7 mg/dL). The area under the curve (AUC) was 19.5% smaller as 14060 mg/dL min compared to the control group (17465 mg/dL min). The result is summarized in Table 61.

TABLE 61

Effect of *Spergularia marina* extract on blood sugar increase in rats due to oral glucose tolerance

| Test group[1] | Blood sugar level with time (mg/dL) | | | | | AUC[2] |
|---|---|---|---|---|---|---|
| | 0 minute | 30 minutes | 60 minutes | 90 minutes | 120 minutes | |
| Control[3] | 65.3 ± 5.9 | 168 ± 22.9 | 176 ± 14.7 | 130 ± 15.1 | 121 ± 11.2 | 17465 ± 1500 |
| *Spergularia marina* extract | 68.8 ± 3.4 | 132 ± 17.4 | 145 ± 22.8 | 128 ± 11.9 | 111 ± 12.3 | 14060 ± 1387 |

[1]Values are mean ± SD (n = 10).
[2]AUC: Area under the curve (area under the blood sugar curve for 120 minutes due to glucose tolerance in min mg/dL unit).
[3]Glucose-administered group.

<3> *Disporum smilacinum* Extract

The *Disporum smilacinum* extract of the present disclosure showed 29.4% less increase in blood sugar level (72.5 mg/dL) as compared to the control group (102.7 mg/dL) after 30 minutes and 23.7% less increase in blood sugar level (84.5 mg/dL) as compared to the control group (110.7 mg/dL). The area under the curve (AUC) was 20% smaller as 13960 mg/dL min compared to the control group (17465 mg/dL min). The result is summarized in Table 62.

TABLE 62

Effect of *Disporum smilacinum* extract on blood sugar increase in rats due to oral glucose tolerance

| Test group[1] | Blood sugar level with time (mg/dL) | | | | | AUC[2] |
|---|---|---|---|---|---|---|
| | 0 minute | 30 minutes | 60 minutes | 90 minutes | 120 minutes | |
| Control[3] | 65.3 ± 5.9 | 168 ± 22.9 | 176 ± 14.7 | 130 ± 15.1 | 121 ± 11.2 | 17465 ± 1500 |
| *Disporum smilacinum* extract | 75.5 ± 2.9 | 148 ± 15.6 | 160 ± 21.0 | 135 ± 8.5 | 120 ± 9.9 | 13960 ± 1111 |

[1]Values are mean ± SD (n = 10).
[2]AUC: Area under the curve (area under the blood sugar curve for 120 minutes due to glucose tolerance in min mg/dL unit).
[3]Glucose-administered group.

<4> *Persicaria posumbu* Extract

The *Persicaria posumbu* extract of the present disclosure showed 24.1% less increase in blood sugar level (78 mg/dL) as compared to the control group (102.7 mg/dL) after 30 minutes and 31.3% less increase in blood sugar level (76 mg/dL) as compared to the control group (110.7 mg/dL). The area under the curve (AUC) was 24.1% smaller as 13249 mg/dL min compared to the control group (17465 mg/dL min). The result is summarized in Table 63.

TABLE 63

Effect of *Persicaria posumbu* extract on blood sugar increase in rats due to oral glucose tolerance

| Test group[1] | Blood sugar level with time (mg/dL) | | | | | AUC[2] |
|---|---|---|---|---|---|---|
| | 0 minute | 30 minutes | 60 minutes | 90 minutes | 120 minutes | |
| Control[3] | 65.3 ± 5.9 | 168 ± 22.9 | 176 ± 14.7 | 130 ± 15.1 | 121 ± 11.2 | 17465 ± 1500 |
| *Persicaria posumbu* extract | 59.0 ± 3.9 | 137 ± 9.8 | 135 ± 12.3 | 118 ± 9.8 | 110 ± 10.1 | 13249 ± 1309 |

[1]Values are mean ± SD (n = 10).
[2]AUC: Area under the curve (area under the blood sugar curve for 120 minutes due to glucose tolerance in min mg/dL unit).
[3]Glucose-administered group.

<5> *Geum aleppicum* Extract

The *Geum aleppicum* extract of the present disclosure showed 40.8% less increase in blood sugar level (60.8 mg/dL) as compared to the control group (102.7 mg/dL) after 30 minutes and 38.8% less increase in blood sugar level (67.8 mg/dL) as compared to the control group (110.7 mg/dL). The area under the curve (AUC) was 38.8% smaller as 13841 mg/dL min compared to the control group (17465 mg/dL min). The result is summarized in Table 64.

TABLE 64

Effect of *Geum aleppicum* extract on blood sugar increase in rats due to oral glucose tolerance

| Test group[1] | Blood sugar level with time (mg/dL) | | | | | AUC[2] |
|---|---|---|---|---|---|---|
| | 0 minute | 30 minutes | 60 minutes | 90 minutes | 120 minutes | |
| Control[3] | 65.3 ± 5.9 | 168 ± 22.9 | 176 ± 14.7 | 130 ± 15.1 | 121 ± 11.2 | 17465 ± 1500 |
| *Geum aleppicum* extract | 64.2 ± 5.1 | 125 ± 9.6 | 132 ± 11.2 | 121 ± 7.1 | 98 ± 5.2 | 13841 ± 984 |

[1]Values are mean ± SD (n = 10).
[2]AUC: Area under the curve (area under the blood sugar curve for 120 minutes due to glucose tolerance in min mg/dL unit).
[3]Glucose-administered group.

3) Effect of Slowing Gastric Emptying Rate (Anti-Obesity Effect)

The change in gastric emptying rate by the extracts was measured It was found out that the extracts can exhibit an anti-obesity effect by increasing the residence time of food in the stomach and thereby reducing food intake.

<1> *Oldenlandia brachypoda* Extract

The administration of the 100, 250, 500 mg/kg *Oldenlandia brachypoda* extracts resulted in decreased gastric emptying rate (see Table 65). Accordingly, it is expected that the *Oldenlandia brachypoda* extract can provide an anti-obesity effect by increasing the residence time of food in the stomach and thereby reducing food intake.

TABLE 65

Effect of gastric emptying rate of *Oldenlandia brachypoda* extract

| Test group | Oral administration dose (mg/kg BW) | Gastric emptying rate (%) |
|---|---|---|
| Control | — | 90 ± 7.4 |
| *Oldenlandia brachypoda* extract | 100 | 78 ± 3.9 |
| | 250 | 55 ± 2.4 |
| | 500 | 34 ± 3.5 |

Control: distilled water-administered group.
Values are means ± SEM (N = 6).

The gastric emptying rate was measured by measuring the amount of phenol red remaining in the stomach 20 minutes after administration of the phenol red. The sample was orally administered 30 minutes before the staining.

As seen from Table 65, the group to which the *Oldenlandia brachypoda* extract was administered slowed the gastric emptying rate in a concentration-dependent manner. Accordingly, it is expected that the extract can provide an anti-obesity effect by increasing the residence time of food in the stomach.

<2> *Spergularia Marina* Extract

The administration of the 100, 250, 500 mg/kg *Spergularia marina* extracts resulted in decreased gastric emptying rate (see Table 66). Accordingly, it is expected that the *Spergularia marina* extract can provide an anti-obesity effect by increasing the residence time of food in the stomach and thereby reducing food intake.

TABLE 66

Effect of gastric emptying rate of *Spergularia marina* extract

| Test group | Oral administration dose (mg/kg BW) | Gastric emptying rate (%) |
|---|---|---|
| Control | — | 90 ± 7.4 |
| *Spergularia marina* extract | 100 | 80 ± 5.1 |
| | 250 | 46 ± 3.3 |
| | 500 | 38 ± 1.9 |

Control: distilled water-administered group.
Values are means ± SEM (N = 6).

The gastric emptying rate was measured by measuring the amount of phenol red remaining in the stomach 20 minutes after administration of the phenol red. The sample was orally administered 30 minutes before the staining.

As seen from Table 66, the group to which the *Spergularia marina* extract was administered slowed the gastric emptying rate in a concentration-dependent manner. Accordingly, it is expected that the extract can provide an anti-obesity effect by increasing the residence time of food in the stomach.

<3> *Disporum smilacinum* Extract

The administration of the 100, 250, 500 mg/kg *Disporum smilacinum* extracts resulted in decreased gastric emptying rate (see Table 67). Accordingly, it is expected that the *Disporum smilacinum* extract can provide an anti-obesity effect by increasing the residence time of food in the stomach and thereby reducing food intake.

TABLE 67

Effect of gastric emptying rate of *Disporum smilacinum* extract

| Test group | Oral administration dose (mg/kg BW) | Gastric emptying rate (%) |
|---|---|---|
| Control | — | 90 ± 7.4 |
| *Disporum smilacinum* extract | 100 | 75 ± 3.9 |
| | 250 | 47 ± 2.8 |
| | 500 | 29 ± 1.9 |

Control: distilled water-administered group.
Values are means ± SEM (N = 6).

The gastric emptying rate was measured by measuring the amount of phenol red remaining in the stomach 20 minutes after administration of the phenol red. The sample was orally administered 30 minutes before the staining.

As seen from Table 67, the group to which the *Disporum smilacinum* extract was administered slowed the gastric emptying rate in a concentration-dependent manner. Accordingly, it is expected that the extract can provide an anti-obesity effect by increasing the residence time of food in the stomach.

<4> *Persicaria posumbu* Extract

The administration of the 100, 250, 500 mg/kg *Persicaria posumbu* extracts resulted in decreased gastric emptying rate (see Table 68). Accordingly, it is expected that the *Persicaria posumbu* extract can provide an anti-obesity effect by increasing the residence time of food in the stomach and thereby reducing food intake.

TABLE 68

Effect of gastric emptying rate of *Persicaria posumbu* extract

| Test group | Oral administration dose (mg/kg BW) | Gastric emptying rate (%) |
|---|---|---|
| Control | — | 90 ± 7.4 |
| *Persicaria posumbu* extract | 100 | 81 ± 0.9 |
| | 250 | 55 ± 2.1 |
| | 500 | 43 ± 1.7 |

Control: distilled water-administered group.
Values are means ± SEM (N = 6).

The gastric emptying rate was measured by measuring the amount of phenol red remaining in the stomach 20 minutes after administration of the phenol red. The sample was orally administered 30 minutes before the staining.

As seen from Table 68, the group to which the *Persicaria posumbu* extract was administered slowed the gastric emptying rate in a concentration-dependent manner. Accordingly, it is expected that the extract can provide an anti-obesity effect by increasing the residence time of food in the stomach.

<5> *Geum aleppicum* Extract

The administration of the 100, 250, 500 mg/kg *Geum aleppicum* extracts resulted in decreased gastric emptying rate (see Table 69). Accordingly, it is expected that the *Geum aleppicum* extract can provide an anti-obesity effect by increasing the residence time of food in the stomach and thereby reducing food intake.

TABLE 69

Effect of gastric emptying rate of *Geum aleppicum* extract

| Test group | Oral administration dose (mg/kg BW) | Gastric emptying rate (%) |
|---|---|---|
| Control | — | 90 ± 7.4 |
| *Geum aleppicum* extract | 100 | 73 ± 4.9 |
| | 250 | 36 ± 2.3 |
| | 500 | 29 ± 0.8 |

Control: distilled water-administered group.
Values are means ± SEM (N = 6).

The gastric emptying rate was measured by measuring the amount of phenol red remaining in the stomach 20 minutes after administration of the phenol red.

As seen from Table 69, the group to which the *Geum aleppicum* extract was administered slowed the gastric emptying rate in a concentration-dependent manner. Accordingly, it is expected that the extract can provide an anti-obesity effect by increasing the residence time of food in the stomach.

4) Measurement of Food Intake (Anti-Obesity Effect)

The anti-obesity effect by the extracts of the present disclosure was investigated.

<1> *Oldenlandia brachypoda* Extract

The effect of the *Oldenlandia brachypoda* extract on food intake was measured 120 minutes after intragastric administration of the *Oldenlandia brachypoda* extract. As a result, the *Oldenlandia brachypoda* extract decreased food intake by 74.2% (see Table 70).

TABLE 70

Effect of *Oldenlandia brachypoda* extract on food intake of rats

| Test group | Oral administration dose (mg/kg BW) | Food intake (g) for 2 hours |
|---|---|---|
| Control | — | 1.9 ± 0.18 |
| *Oldenlandia brachypoda* extract | 500 | 0.49 ± 0.01 |

As seen from Table 70, the group to which the *Oldenlandia brachypoda* extract was administered showed much less food intake for 2 hours as compared to the control group. Accordingly, it is expected that the *Oldenlandia brachypoda* extract will provide a superior anti-obesity effect.

<2> *Spergularia Marina* Extract

The effect of the *Spergularia marina* extract on food intake was measured 120 minutes after intragastric administration of the *Spergularia marina* extract. As a result, the *Spergularia marina* extract decreased food intake by 72% (see Table 71).

TABLE 71

Effect of *Spergularia marina* extract on food intake of rats

| Test group | Oral administration dose (mg/kg BW) | Food intake (g) for 2 hours |
|---|---|---|
| Control | — | 1.9 ± 0.18 |
| *Spergularia marina* extract | 500 | 0.54 ± 0.21 |

As seen from Table 71, the group to which the *Spergularia marina* extract was administered showed much less food intake for 2 hours as compared to the control group. Accordingly, it is expected that the *Spergularia marina* extract will provide a superior anti-obesity effect.

<3> *Disporum smilacinum* Extract

The effect of the *Disporum smilacinum* extract on food intake was measured 120 minutes after intragastric administration of the *Disporum smilacinum* extract. As a result, the *Disporum smilacinum* extract decreased food intake by 68% (see Table 72).

TABLE 72

Effect of *Disporum smilacinum* extract on food intake of rats

| Test group | Oral administration dose (mg/kg BW) | Food intake (g) for 2 hours |
| --- | --- | --- |
| Control | — | 1.9 ± 0.18 |
| *Disporum smilacinum* extract | 500 | 0.61 ± 0.09 |

As seen from Table 72, the group to which the *Disporum smilacinum* extract was administered showed much less food intake for 2 hours as compared to the control group. Accordingly, it is expected that the *Disporum smilacinum* extract will provide a superior anti-obesity effect.

<4> *Persicaria posumbu* Extract

The effect of the *Persicaria posumbu* extract on food intake was measured 120 minutes after intragastric administration of the *Persicaria posumbu* extract. As a result, the *Persicaria posumbu* extract decreased food intake by 67.9% (see Table 73).

TABLE 73

Effect of *Persicaria posumbu* extract on food intake of rats

| Test group | Oral administration dose (mg/kg BW) | Food intake (g) for 2 hours |
| --- | --- | --- |
| Control | — | 1.9 ± 0.18 |
| *Persicaria posumbu* extract | 500 | 0.61 ± 0.08 |

As seen from Table 73, the group to which the *Persicaria posumbu* extract was administered showed much less food intake for 2 hours as compared to the control group. Accordingly, it is expected that the *Persicaria posumbu* extract will provide a superior anti-obesity effect.

<5> *Geum aleppicum* Extract

The effect of the *Geum aleppicum* extract on food intake was measured 120 minutes after intragastric administration of the *Geum aleppicum* extract. As a result, the *Geum aleppicum* extract decreased food intake by 79.5% (see Table 74).

TABLE 74

Effect of *Geum aleppicum* extract on food intake of rats

| Test group | Oral administration dose (mg/kg BW) | Food intake (g) for 2 hours |
| --- | --- | --- |
| Control | — | 1.9 ± 0.18 |
| *Geum aleppicum* extract | 500 | 0.39 ± 0.05 |

As seen from Table 74, the group to which the *Geum aleppicum* extract was administered showed much less food intake for 2 hours as compared to the control group. Accordingly, it is expected that the *Geum aleppicum* extract will provide a superior anti-obesity effect.

5) Effect on Chloride Excretion (Effect of Promoting Digestion)

The effect of the extracts of the present disclosure on gastric acid secretion was investigated. It was confirmed that the extracts of the present disclosure can promote digestion by stimulating gastric acid secretion.

<1> *Oldenlandia brachypoda* Extract

Chloride concentration in rat serum was measured in order to evaluate the effect of the *Oldenlandia brachypoda* extract on gastric acid secretion indirectly. When blood chloride level was measured 30 minutes after oral administration of the *Oldenlandia brachypoda* extract (500 mg/kg BW), the *Oldenlandia brachypoda* extract increased the chloride concentration in serum by 12.8% as compared to the control group (see Table 75). Accordingly, is expected that the extract can promote digestion.

TABLE 75

Effect of *Oldenlandia brachypoda* extract on chloride concentration in rat serum

| Test group | Oral administration dose (mg/kg BW) | Serum chloride level (mg/dL) |
| --- | --- | --- |
| Control | — | 265 ± 19.1 |
| *Oldenlandia brachypoda* extract | 500 | 299 ± 11.7 |

As seen from Table 75, the rats to which the *Oldenlandia brachypoda* extract was administered showed higher serum chloride level. Accordingly, is expected that the *Oldenlandia brachypoda* extract can promote digestion by promoting gastric acid secretion.

<2> *Spergularia Marina* Extract

Chloride concentration in rat serum was measured in order to evaluate the effect of the *Spergularia marina* extract on gastric acid secretion indirectly. When blood chloride level was measured 30 minutes after oral administration of the *Spergularia marina* extract (500 mg/kg BW), the *Spergularia marina* extract increased the chloride concentration in serum by 21% as compared to the control group (see Table 76). Accordingly, is expected that the extract can promote digestion.

TABLE 76

Effect of *Spergularia marina* extract on chloride concentration in rat serum

| Test group | Oral administration dose (mg/kg BW) | Serum chloride level (mg/dL) |
| --- | --- | --- |
| Control | — | 265 ± 19.1 |
| *Spergularia marina* extract | 500 | 321 ± 21.4 |

As seen from Table 76, the rats to which the *Spergularia marina* extract was administered showed higher serum chloride level. Accordingly, is expected that the *Spergularia marina* extract can promote digestion by promoting gastric acid secretion.

<3> *Disporum smilacinum* Extract

Chloride concentration in rat serum was measured in order to evaluate the effect of the *Disporum smilacinum* extract on gastric acid secretion indirectly. When blood chloride level was measured 30 minutes after oral administration of the *Disporum smilacinum* extract (500 mg/kg BW), the *Disporum smilacinum* extract increased the chloride concentration in serum by 52.8% as compared to the control group (see Table 77). Accordingly, is expected that the extract can promote digestion.

TABLE 77

Effect of *Disporum smilacinum* extract on chloride concentration in rat serum

| Test group | Oral administration dose (mg/kg BW) | Serum chloride level (mg/dL) |
|---|---|---|
| Control | — | 265 ± 19.1 |
| *Disporum smilacinum* extract | 500 | 405 ± 30.7 |

As seen from Table 77, the rats to which the *Disporum smilacinum* extract was administered showed higher serum chloride level. Accordingly, is expected that the *Disporum smilacinum* extract can promote digestion by promoting gastric acid secretion.

<4> *Persicaria posumbu* Extract

Chloride concentration in rat serum was measured in order to evaluate the effect of the *Persicaria posumbu* extract on gastric acid secretion indirectly. When blood chloride level was measured 30 minutes after oral administration of the *Persicaria posumbu* extract (500 mg/kg BW), the *Persicaria posumbu* extract increased the chloride concentration in serum by 12.5% as compared to the control group (see Table 78). Accordingly, is expected that the extract can promote digestion.

TABLE 78

Effect of *Persicaria posumbu* extract on chloride concentration in rat serum

| Test group | Oral administration dose (mg/kg BW) | Serum chloride level (mg/dL) |
|---|---|---|
| Control | — | 265 ± 19.1 |
| *Persicaria posumbu* extract | 500 | 298 ± 10.4 |

As seen from Table 78, the rats to which the *Persicaria posumbu* extract was administered showed higher serum chloride level. Accordingly, is expected that the *Persicaria posumbu* extract can promote digestion by promoting gastric acid secretion.

<5> *Geum aleppicum* Extract

Chloride concentration in rat serum was measured in order to evaluate the effect of the *Geum aleppicum* extract on gastric acid secretion indirectly. When blood chloride level was measured 30 minutes after oral administration of the *Geum aleppicum* extract (500 mg/kg BW), the *Geum aleppicum* extract increased the chloride concentration in serum by 33.6% as compared to the control group (see Table 79). Accordingly, is expected that the extract can promote digestion.

TABLE 79

Effect of *Geum aleppicum* extract on chloride concentration in rat serum

| Test group | Oral administration dose (mg/kg BW) | Serum chloride level (mg/dL) |
|---|---|---|
| Control | — | 265 ± 19.1 |
| *Geum aleppicum* extract | 500 | 354 ± 18.5 |

As seen from Table 79, the rats to which the *Geum aleppicum* extract was administered showed higher serum chloride level. Accordingly, is expected that the *Geum aleppicum* extract can promote digestion by promoting gastric acid secretion.

The invention claimed is:

1. A method of stimulating secretion of glucagon-like peptide-1 (GLP-1) in a subject in need thereof, the method comprising:
   administering to the subject an effective amount of a composition comprising at least one of a *Disporum smilacinum* hydro-ethanolic extract, a *Persicaria posumbu* hydro-ethanolic extract and a *Geum aleppicum* hydro-ethanolic extract.

2. The method of claim 1, wherein the subject is diagnosed with a disorder selected from the group consisting of: diabetes, obesity, a digestive disorder, gastrointestinal malabsorption, a liver disease, a heart disease and arteriosclerosis.

3. A method of stimulating secretion of cholecystokinin (CCK) in a subject in need of such stimulation, the method comprising:
   administering to the subject an effective amount of a composition comprising at least one of a *Disporum smilacinum* hydro-ethanolic extract, a *Persicaria posumbu* hydro-ethanolic extract and a *Geum aleppicum* hydro-ethanolic extract.

4. The method of claim 3, wherein the subject is diagnosed with a disorder selected from the group consisting of: diabetes, obesity, a digestive disorder, gastrointestinal malabsorption, a liver disease, a heart disease and arteriosclerosis.

5. A method of stimulating secretion of 5-hydroxytryptamine (5-HT) in a subject in need of such stimulation, the method comprising:
   administering to the subject an effective amount of a composition comprising at least one of a *Disporum smilacinum* hydro-ethanolic extract, a *Persicaria posumbu* hydro-ethanolic extract and a *Geum aleppicum* hydro-ethanolic extract.

6. The method of claim 5, wherein the subject is diagnosed with a disorder selected from the group consisting of: diabetes, obesity, a digestive disorder, gastrointestinal malabsorption, a liver disease, a heart disease and arteriosclerosis.

7. A method of activing hTGR5 (human TGR5 (G protein-coupled bile acid receptor 131, GPR131)) in a subject in need thereof, the method comprising:
   administering, to a subject, a composition comprising at least one of a *Disporum smilacinum* hydro-ethanolic extract, a *Persicaria posumbu* ethanolic hydro-ethanolic and a *Geum aleppicum* hydro-ethanolic extract.

8. The method of claim 7, wherein the subject is diagnosed with a disorder selected from the group consisting of: diabetes, obesity, a digestive disorder, gastrointestinal malabsorption, a liver disease, a heart disease and arteriosclerosis.

* * * * *